US006955817B2

(12) United States Patent
McAtee et al.

(10) Patent No.: US 6,955,817 B2
(45) Date of Patent: *Oct. 18, 2005

(54) CLEANSING ARTICLES FOR SKIN OR HAIR

(75) Inventors: David M. McAtee, Mason, OH (US); Erik J. Hasenoehrl, Loveland, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 10/236,832

(22) Filed: Sep. 6, 2002

(65) Prior Publication Data

US 2003/0113364 A1 Jun. 19, 2003

Related U.S. Application Data

(60) Division of application No. 09/884,240, filed on Jun. 18, 2001, now Pat. No. 6,495,151, which is a division of application No. 09/318,676, filed on May 25, 1999, now Pat. No. 6,280,757, which is a continuation-in-part of application No. 09/152,034, filed on Sep. 11, 1998, now Pat. No. 6,153,208, which is a continuation-in-part of application No. 09/148,540, filed on Sep. 4, 1998, now Pat. No. 6,190,678, which is a continuation-in-part of application No. 09/065,991, filed on Apr. 24, 1998, now abandoned, which is a continuation-in-part of application No. 08/861,750, filed on May 22, 1997, now Pat. No. 6,132,746.

(51) Int. Cl.$^7$ ............................ A61K 7/50; A61K 7/075
(52) U.S. Cl. ................... 424/402; 424/401; 424/70.1; 424/70.19; 424/70.21; 424/70.22; 424/70.31
(58) Field of Search .................... 424/402, 401, 424/70.1, 70.19, 70.21, 70.22, 70.31, 409

(56) References Cited

U.S. PATENT DOCUMENTS

| | | |
|---|---|---|
| 2,877,115 A | 3/1959 | Wemyes, Jr. et al. |
| 2,944,931 A | 7/1960 | Yang |
| 3,306,392 A | 2/1967 | Britt |
| 3,424,643 A | 1/1969 | Lewis, Jr. et al. |
| 3,451,758 A | 6/1969 | McClain |
| 3,580,853 A | 5/1971 | Parran |
| 3,632,398 A | 1/1972 | Perez-Zamora |
| 3,688,025 A | 8/1972 | Morton |
| 3,795,624 A | 3/1974 | Feinstone |
| 3,895,128 A | 7/1975 | Gaiser |
| 3,896,807 A | 7/1975 | Buchalter |
| 3,939,260 A | 2/1976 | Lafon |
| 3,944,694 A | 3/1976 | McQueary |
| 3,949,137 A | 4/1976 | Akrongold et al. |
| 3,956,551 A | 5/1976 | Richards |
| 3,994,771 A | 11/1976 | Morgan, Jr. et al. |
| 4,112,167 A | 9/1978 | Dake et al. |
| 4,127,515 A | 11/1978 | MacRae et al. |
| 4,145,302 A | 3/1979 | Doan |
| 4,206,195 A | 6/1980 | Bolich, Jr. et al. |
| 4,206,196 A | 6/1980 | Davis |
| 4,271,272 A | 6/1981 | Strickman et al. |
| 4,303,543 A | 12/1981 | Mansy |
| 4,343,403 A | 8/1982 | Daniels et al. |
| 4,397,754 A | 8/1983 | Collishaw et al. |
| 4,462,981 A | 7/1984 | Smith |
| 4,515,703 A | 5/1985 | Haq |
| 4,525,411 A | 6/1985 | Schmidt |
| 4,553,275 A | 11/1985 | Goldstein |
| 4,559,157 A | 12/1985 | Smith et al. |
| 4,574,052 A | 3/1986 | Gupte et al. |
| 4,603,069 A | 7/1986 | Haq et al. |
| 4,683,001 A | 7/1987 | Floyd et al. |
| 4,690,821 A | 9/1987 | Smith et al. |
| 4,725,657 A | 2/1988 | Shibanai |
| 4,735,739 A | 4/1988 | Floyd et al. |
| 4,758,467 A | 7/1988 | Lempriere |
| 4,788,060 A | 11/1988 | Endicott et al. |
| 4,803,195 A | 2/1989 | Holzner |
| 4,806,572 A | 2/1989 | Kellett |
| 4,856,541 A | 8/1989 | Kellett et al. |
| 4,865,221 A | 9/1989 | Jackson et al. |
| 4,882,221 A | 11/1989 | Bogart et al. |
| 4,891,227 A | 1/1990 | Thaman et al. |
| 4,891,228 A | 1/1990 | Thaman et al. |
| 4,904,524 A | 2/1990 | Yoh |
| 4,946,617 A | 8/1990 | Sheridan et al. |
| 4,948,585 A | 8/1990 | Schlein |
| 5,017,365 A | 5/1991 | Niedbala |
| 5,063,062 A | 11/1991 | Greenspan et al. |
| 5,091,102 A | 2/1992 | Sheridan |
| 5,112,612 A | 5/1992 | Garvey et al. |
| 5,139,687 A | 8/1992 | Borgher, Sr. et al. |
| 5,185,155 A | 2/1993 | Behan et al. |
| 5,232,613 A | 8/1993 | Bacon et al. |

(Continued)

FOREIGN PATENT DOCUMENTS

| | | |
|---|---|---|
| CN | 1050066 A | 3/1991 |
| CN | 1102211 A | 5/1995 |
| CN | 1106704 A | 8/1995 |

(Continued)

OTHER PUBLICATIONS

Vaughan, C.D., "Solubility Effects in Product Package, Penetration, and Preservation", Cosmetics & Toiletries, vol. 103, pp. 47–69 (Oct. 1988).
DIN 53 902.
EN 12728.

(Continued)

Primary Examiner—Jyothsna Venkat
(74) Attorney, Agent, or Firm—Jason J. Camp; Brian M. Bolam; Tara M. Rosnell

(57) ABSTRACT

The present invention relates to disposable, personal cleansing articles useful for cleansing the skin or hair. These articles are used by the consumer by wetting the dry article with water and then rubbing the article against the skin or hair. The article comprises a water insoluble substrate having a cleansing surface that contains apertures of a certain size and frequency, and a lathering surfactant releasably associated with the substrate. Preferably, the articles of the present invention further comprise a conditioning component.

54 Claims, 4 Drawing Sheets

U.S. PATENT DOCUMENTS

| | | |
|---|---|---|
| 5,236,615 A | 8/1993 | Trinh et al. |
| 5,246,611 A | 9/1993 | Trinh |
| 5,250,728 A | 10/1993 | Parker et al. |
| 5,254,109 A | 10/1993 | Smith et al. |
| 5,284,972 A | 2/1994 | Parker et al. |
| 5,292,533 A | 3/1994 | McMahon et al. |
| 5,302,446 A | 4/1994 | Horn |
| 5,348,667 A | 9/1994 | Bacon et al. |
| 5,376,287 A | 12/1994 | Borcher, Sr. et al. |
| 5,449,822 A | 9/1995 | Parker et al. |
| 5,466,460 A | 11/1995 | McMahon et al. |
| 5,525,345 A | 6/1996 | Warner et al. |
| 5,538,732 A | 7/1996 | Smith et al. |
| 5,552,206 A | 9/1996 | Knoke et al. |
| 5,552,378 A | 9/1996 | Trinh et al. |
| 5,605,749 A | 2/1997 | Pike et al. |
| 5,620,694 A | 4/1997 | Girardot |
| 5,621,008 A | 4/1997 | Ptchelintsev |
| 5,648,083 A | 7/1997 | Blieszner et al. |
| 5,661,170 A | 8/1997 | Chodosh |
| 5,683,971 A | 11/1997 | Rose et al. |
| 5,698,475 A | 12/1997 | Vlasblom |
| 5,702,992 A | 12/1997 | Martin et al. |
| 5,750,122 A | 5/1998 | Evans et al. |
| 5,814,188 A | 9/1998 | Vinson et al. |
| 5,821,215 A | 10/1998 | Crudden et al. |
| 5,837,664 A | 11/1998 | Black |
| 5,866,110 A | 2/1999 | Moore et al. |
| 5,869,441 A | 2/1999 | Fair et al. |
| 5,871,762 A | 2/1999 | Venkitaraman et al. |
| 5,914,177 A | 6/1999 | Smith, III et al. |
| 5,951,991 A | 9/1999 | Wagner et al. |
| 5,971,841 A | 10/1999 | Tintelnot |
| 5,972,361 A * | 10/1999 | Fowler et al. ............... 424/402 |
| 5,980,931 A * | 11/1999 | Fowler et al. ............... 424/443 |
| 5,993,504 A | 11/1999 | Nonomura et al. |
| 6,054,450 A | 4/2000 | Shin et al. |
| 6,060,149 A | 5/2000 | Cabell et al. |
| 6,063,390 A | 5/2000 | Farrell et al. |
| 6,063,397 A * | 5/2000 | Fowler et al. ............... 424/443 |
| 6,074,655 A * | 6/2000 | Fowler et al. ............... 424/402 |
| 6,087,452 A | 7/2000 | Stewart et al. |
| 6,099,776 A | 8/2000 | Tintelnot |
| 6,103,644 A | 8/2000 | Sheridan |
| 6,132,746 A * | 10/2000 | Hasenoehrl et al. ......... 424/402 |
| 6,132,841 A | 10/2000 | Guthrie et al. |
| 6,153,208 A * | 11/2000 | McAtee et al. ............. 424/402 |
| 6,156,323 A | 12/2000 | Verdicchio et al. |
| 6,190,678 B1 * | 2/2001 | Hasenoehrl et al. ......... 424/401 |
| 6,217,889 B1 | 4/2001 | Lorenzi et al. |
| 6,242,411 B1 | 6/2001 | D'Ambrogio et al. |
| 6,280,757 B1 * | 8/2001 | McAtee et al. ............. 424/402 |
| 6,338,855 B1 * | 1/2002 | Albacarys et al. .......... 424/409 |
| 6,391,835 B1 | 5/2002 | Gott et al. |
| 6,422,933 B1 | 7/2002 | Tintelnot |
| 6,491,937 B1 | 12/2002 | Slavtcheff et al. |
| 6,495,151 B2 * | 12/2002 | McAtee et al. ............. 424/402 |
| 6,579,158 B2 | 6/2003 | Tintelnot |
| 6,616,641 B2 | 9/2003 | Sheridan |
| 6,638,527 B2 | 10/2003 | Gott et al. |
| 2001/0041529 A1 | 11/2001 | Tintelnot |
| 2001/0046513 A1 | 11/2001 | Gott et al. |
| 2003/0022572 A1 | 1/2003 | Gott et al. |
| 2003/0199838 A1 | 10/2003 | Sheridan |
| 2003/0228352 A1 | 12/2003 | Hasenoehrl et al. |

FOREIGN PATENT DOCUMENTS

| | | |
|---|---|---|
| CN | 1135320 A | 11/1996 |
| DE | 24 02 730 | 7/1975 |
| DE | 24 60 239 | 7/1975 |
| DE | 24 37 165 | 1/1976 |
| EP | 0186208 A | 7/1986 |
| EP | 0353013 A2 | 1/1990 |
| EP | 0485212 A1 | 5/1992 |
| EP | 0550067 B1 | 7/1993 |
| EP | 0613675 A1 | 9/1994 |
| EP | 0615720 A1 | 9/1994 |
| EP | 0 834 307 A2 | 4/1998 |
| EP | 0 976 392 A1 | 2/2000 |
| FR | 2271808 | 12/1975 |
| FR | 2538238 | 6/1984 |
| GB | 0 840 399 A | 7/1960 |
| GB | 1577926 | 10/1980 |
| GB | 2163947 A | 3/1986 |
| GB | 2218430 A | 11/1989 |
| GB | 2297490 A | 8/1996 |
| JP | 66-75500 A | 6/1980 |
| JP | 58-112542 | 7/1983 |
| JP | 63-097699 | 4/1988 |
| JP | 01-246478 | 10/1989 |
| JP | 5-117699 A2 | 5/1993 |
| JP | 08-141012 | 6/1996 |
| JP | 09-151400 | 6/1997 |
| JP | 09-216809 | 8/1997 |
| WO | WO 89/03639 A1 | 5/1989 |
| WO | WO 93/05141 A1 | 3/1993 |
| WO | WO 93/21899 A1 | 11/1993 |
| WO | WO 94/02674 A1 | 2/1994 |
| WO | WO 94/27569 A1 | 12/1994 |
| WO | WO 95/00116 A2 | 1/1995 |
| WO | WO 95/16824 A1 | 6/1995 |
| WO | WO 96/14835 A1 | 10/1995 |
| WO | WO 95/31189 A1 | 11/1995 |
| WO | WO 96/04937 A1 | 2/1996 |
| WO | WO 96/06595 A1 | 3/1996 |
| WO | WO 96/24329 A1 | 8/1996 |
| WO | WO 96/24723 A1 | 8/1996 |
| WO | WO 96/34036 A1 | 11/1996 |
| WO | WO 96/36315 A1 | 11/1996 |
| WO | WO 97/00001 A2 | 1/1997 |
| WO | WO 97/07781 A1 | 3/1997 |
| WO | WO 97/16068 A1 | 5/1997 |
| WO | WO 97/40126 A1 | 10/1997 |
| WO | WO 97/45258 A1 | 12/1997 |
| WO | WO 99/13861 A1 | 3/1999 |
| WO | WO 99/37476 A1 | 7/1999 |
| WO | WO 01/13880 A1 | 3/2001 |
| WO | WO 01/35923 A1 | 5/2001 |
| WO | WO 03/44153 A1 | 5/2003 |
| WO | WO 03/63807 A1 | 8/2003 |

OTHER PUBLICATIONS

Rompp Chemie Lexikon, 9. Auflage, Georg Thieme Verlag, Stuttgart, 1990, Stichwort: Harte des Wassers.

A. Domsch, Die kosmetischen Praparate, Band 2, 4. Auflage, Verlag fur chem . . . Industrie, H. Ziolkowsky KG, Augsburg, 1992, Kap. 3.1.

Blue Apertured Cloth (see attached three letters to Unilever).

Tender Bath, Westgate Laboratories, Edison, NJ, 1987, (Product Description—product believed to have been test marketed In Sep., 1986).

Buf–Puf Singles Skin Conditioning, labeling, copyright 1991.

Buf–Puf Singles Oil–Free, Labelling, copyright 1991.

Buf–Puf Singles With Cleanser for Normal to Dry Skin, labeling, copyright 1996.

Buf–Puf Singles With Cleanser for Normal to Oily Skin, labeling, copyright 1995.
Buf–Puf article photocopied actual size.

Test records.

* cited by examiner

CLEANSING ARTICLES FOR SKIN OR HAIR

CROSS-REFERENCE TO RELATED APPLICATIONS

This application is a divisional patent application of divisional U.S. application Ser. No. 09/884,240, filed Jun. 18, 2001 now U.S. Pat. No. 6,495,151, which is a divisional of application Ser. No. 09/318,676, filed May 25, 1999 now U.S. Pat. No. 6,280,757, granted Aug. 28, 2001, which is a continuation-in-part (CIP) of application Ser. No. 09/152,034, filed Sep. 11, 1998 now U.S. Pat. No. 6,153,208, granted Nov. 28, 2000, which is a CIP of application Ser. No. 09/148,540, filed Sep. 4, 1998 now U.S. Pat. No. 6,190,678, granted Feb. 20, 2001, which is a CIP of U.S. Ser. No. 09/065,991, filed Apr. 24, 1998, now abandoned, which is a CIP of application Ser. No. 08/861,750, filed May 22, 1997, now U.S. Pat. No. 6,132,746, granted Oct. 17, 2000.

TECHNICAL FIELD

The present invention relates to disposable personal cleansing articles useful for cleansing, and optionally conditioning, the skin or hair, and more particularly to a disposable cleansing, article having a substrate, comprising either single or multiple layers, which contains a plurality of apertures along with a lathering surfactant component. These articles are used by the consumer by wetting the article, which may be dry, with water and by thereafter forming a lather by rubbing the article against itself and/or against skin or hair.

BACKGROUND OF THE INVENTION

Personal cleansing products have traditionally been marketed in a variety of forms such as bar soaps, creams, lotions, and gels. These cleansing formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use. Personal cleansing products are frequently used with, or marketed in the form of, articles that employ a substrate or other implement that carries a cleansing material or is used to deliver a cleansing material to the skin or hair.

Traditional forms of personal cleansing products and articles may be very useful for providing efficacious cleansing and lathering. Such conventional products and articles, however are less suitable for also simultaneously providing other desirable effects such as delivering a skin or hair conditioning benefit. One solution to this problem is to use separate cleansing and conditioning products or articles. However, this is not always convenient or practical, and many consumers would prefer to use a single article which can both cleanse and condition the skin or hair. In a typical cleansing composition or product, the conditioning ingredients are difficult to formulate because many conditioners are incompatible with the surfactants, resulting in an undesirable non-homogenous mixture. To obtain a homogeneous mixture with conditioning ingredients, and to prevent the loss of conditioning ingredients before deposition, additional ingredients, e.g. emulsifiers, thickeners, and gellants are often added to suspend the conditioning ingredients within a surfactant mixture. This results in an aesthetically pleasing homogenous mixture, but often results in poor deposition of conditioning ingredients onto skin or hair because the conditioners are emulsified and not efficiently released during cleansing. Also, many conditioning agents have the disadvantage of suppressing lather generation. Lather suppression is a problem because many consumers seek cleansing articles that provide a rich, creamy, and generous lather.

Therefore, it is seen that conventional cleansing products and articles which attempt to combine surfactants and other materials such as conditioning ingredients suffer from disadvantages inherently resulting from the incompatibilities of surfactants and conditioners. A need clearly exists to develop cleansing systems which provide effective cleansing, effective lathering and yet can also, if desired, consistently provide other benefits such as sufficient conditioning in a single article.

It is also highly desirable to deliver cleansing and preferably conditioning benefits from a disposable, single use article. Disposable articles are convenient because they obviate the need to carry cumbersome bottles, bars, jars, tubes, and other forms of both cleansing and conditioning articles. Disposable articles are also a more sanitary alternative to the use of a sponge, washcloth, or other cleansing implement intended for multiple reuse, because such implements develop bacterial growth, unpleasant odors, and other undesirable characteristics related to repeated use.

Accordingly, it is an object of the present invention to provide washcloth-like articles for cleansing, and preferably also, conditioning the skin or hair when the articles are used wetted with water and rubbed against the skin or hair.

It is another object of the present invention to provide such cleansing articles which are disposable and intended for single use.

It is another object of the present invention to provide such cleansing articles which are mild to the skin or hair.

It is another object of the present invention to provide such cleansing articles which, upon wetting, are capable of generating especially desirable amounts of lather.

SUMMARY OF THE INVENTION

The present invention relates to disposable, single use personal cleansing articles especially useful for cleansing facial skin. Each such article comprises a) a water-insoluble, non-woven substrate having at least one cleansing surface; and b) from about 0.5% to 250% by weight of the substrate of a lathering surfactant which is releasably associated with the substrate. The cleansing surface of the substrate contains a plurality of apertures which range in size from about 0.5 mm to 5 mm in diameter. These apertures are located within said cleansing surface of the substrate at a frequency of from about 0.5–12 apertures per linear centimeter. Preferred multiple layer cleansing articles of this invention utilize a two-ply substrate wherein one or both plies are apertured. Also preferably at least one of the plies of the substrate is wet extensible and the second ply is less wet extensible than the first ply. Preferred articles are also substantially dry prior to use and contain one or more water-soluble or water-insoluble conditioning agents in addition to the lathering surfactant component.

The present invention also relates to methods for manufacturing cleansing articles of the configuration describe herein. Also, the present invention provides methods for cleansing, and optionally conditioning, the skin or hair using the articles described herein.

DETAILED DESCRIPTION OF THE INVENTION

Figure 1:
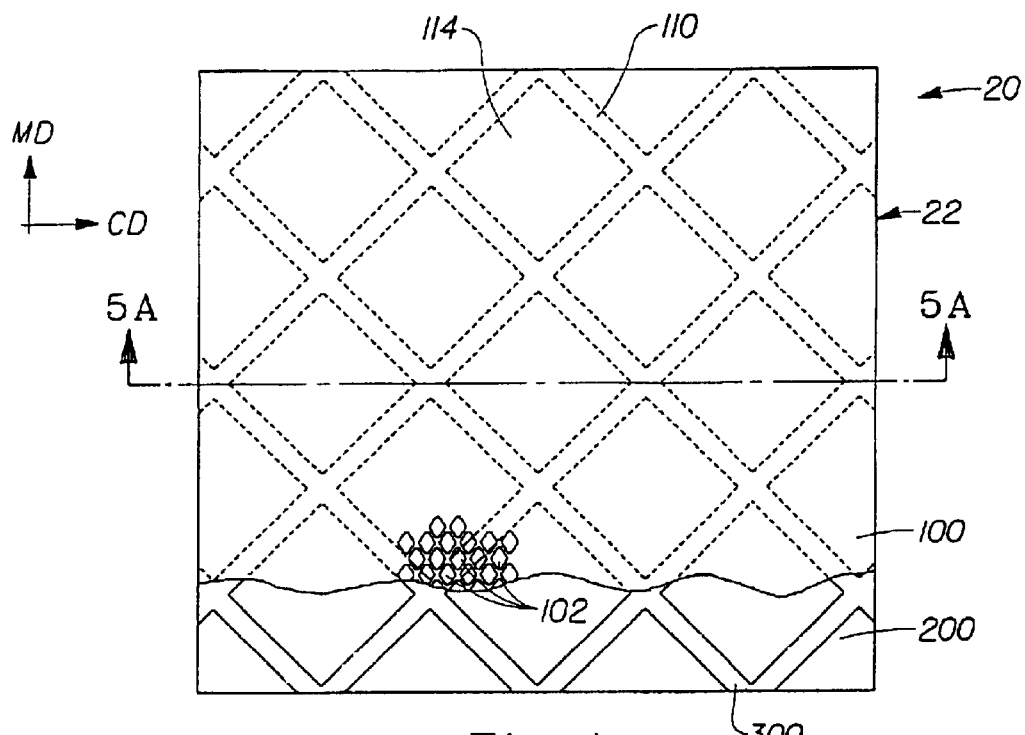
FIG. 1 is a plan view illustration of one embodiment of a cleansing article of the present invention, the article including an extensible, apertured first layer and a less extensible second layer, with the first layer shown facing the viewer, and with a portion of the first layer shown cut away to show a continuous network of generally parallel sets of intersecting lines of adhesive which serve to bond the first layer to the second layer, the bonded region defining generally diamond-shaped unbonded regions.

The essential elements of cleansing articles of the present invention, i.e., the apertured water-insoluble substrate and the lathering surfactant, as well as a wide variety of optional elements, are described in detail as follows. All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

By a "lathering surfactant" is meant a surfactant, which when combined with water and mechanically agitated generates a foam or lather. Preferably, these surfactants should be mild, which means that these surfactants provide sufficient cleansing or detersive benefits but do not overly dry the skin or hair (e.g., removing too much natural oil and/or moisture), and yet meet the lathering criteria described above.

The term "lathering product" or "lathering article," as used herein, means that the product or article contains enough of the surfactants described herein that it can generate $\geq 30$ ml of Lather Volume, as described herein in the Lather Volume Test. These Lather Volume measurements are conducted with a medium hardness water (8–10 grains per gallon) at 95° C.

The terms "disposable" or "single use", are used herein in their ordinary sense to mean a article that is disposed or discarded after one usage event.

The term "conditioning component," as used herein, means a combination of the conditioning agents.

The term "water-activated," as used herein, means that the present invention is presented to the consumer in dry form to be used after it is wetted with water. It is found that these articles produce a lather or are "activated" by contacting them with water and then further subjecting the article to mechanical forces, such as rubbing.

The term "substantially dry," as used herein, means that prior to use the article is substantially free of water and generally feels dry to the touch. Thus, the articles of the present invention will generally comprise less than about 10% by weight of water, preferably less than about 5% by weight of water, and more preferably less than about 1% by weight of water, the forgoing measured in a dry environment, e.g., low humidity. One of ordinary skill in the art would recognize that the water content of a article such as in the present invention can vary with the relative humidity of the environment.

The term "mild" as used herein in reference to the lathering surfactants and articles of the present invention means that the articles of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H$—$H_2O$) which passes from the test solution through the skin epidermis into the physiological buffer contained in the diffusate chamber. This test is described by T. J. Franz in the J. Invest. Dermatol., 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

The personal cleansing articles of the present invention comprise the following essential components: (A) a water-insoluble substrate, wherein at least a portion of said substrate contains apertures, and (B) at least one lathering surfactant added onto or impregnated into the substrate. The articles of the present invention can further optionally comprise a conditioning component added onto or impregnated into the substrate.

Apertured Water Insoluble Substrate

The products of the present invention comprise a water insoluble substrate having at least one cleansing surface. By "water insoluble" is meant that the substrate does not dissolve in or readily break apart upon immersion in water. The water insoluble substrate is the implement or vehicle for delivering the lathering surfactant and optionally the conditioning component of the present invention to the skin or hair to be cleansed and conditioned. Without being limited by theory, it is believed that the substrate, by providing mechanical forces and agitation provides a lather generating effect and also aids in the deposition of the conditioning component.

A wide variety of materials can be used as the substrate. The following nonlimiting characteristics are desirable: (i)

sufficient wet strength for use, (ii) sufficient abrasivity, (iii) sufficient loft and porosity, (iv) sufficient thickness, and (v) appropriate size.

Nonlimiting examples of suitable insoluble substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By nonwoven is meant that the layer is comprised of fibers which are not woven into a fabric but rather are formed into a sheet, mat, or pad layer. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," *Nonwoven World* (1987); *The Encyclopedia Americana,* vol. 11, pp. 147–153, and vol. 26, pp. 566–581 (1984); U.S. Pat. No. 4,891,227, to Thaman et al., issued Jan. 2, 1990; and U.S. Pat. No. 4,891,228 which are all incorporated by reference herein in their entirety.

Nonwoven substrates made from natural materials consist of webs or sheets most commonly formed on a fine wire screen from a liquid suspension of the fibers. See C. A. Hampel et al., *The Encyclopedia of Chemistry,* third edition, 1973, pp. 793–795 (1973); *The Encyclopedia Americana,* vol. 21, pp. 376–383 (1984); and G. A. Smook, *Handbook of Pulp and Paper Technologies,* Technical Association for the Pulp and Paper Industry (1986); which are incorporated by reference herein in their entirety.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 85 grams per square meter, available from James River, Green Bay, Wis.; and Walkisoft®, an embossed airlaid cellulosic having a base weight of about 90 grams per square meter, available from Walkisoft U.S.A., Mount Holly, N.C.

Methods of making nonwoven substrates, including apertured substrates, are well known in the art. Generally, these nonwoven substrates can be made by air-laying, water-laying, meltblowing, coforming, spinbonding, or carding processes in which the fibers or filaments are first cut to desired lengths from long strands, passed into a water or air stream, and then deposited onto a screen or belt through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates used in the present invention can consist of a single layer or multiple layers. In addition, a multilayered substrate can include films and other nonfibrous materials.

The substrates used to form the personal cleansing articles of the present invention must contain apertures or openings in the cleansing surface of the substrate. Such apertures may be generally circular in shape or may be openings of other shapes, including squares, rectangles, trapezoids, diamonds, hexagons, irregular shapes and the like. Such apertures need not be uniform in size and shape, but preferably will be substantially uniform in both size and shape.

The apertures in the cleansing surface of the substrate will generally range in average diameter between about 0.5 mm and 5 mm. More preferably, the apertures will range in size between about 1 mm to 4 mm in average diameter. Preferably no more than about 10% of the apertures in the cleansing surface of the substrate will fall outside these size ranges. More preferably no more than about 5% of the apertures in the cleansing surface will fall outside these size ranges. For apertures which are not circular in shape, the "diameter" of the aperture refers to the diameter of a circular opening having the same surface area as the opening of the non-circular shaped aperture.

Within the cleansing surface of the substrate, the apertures will generally occur at a frequency of from about 0.5 to 12 apertures per straight linear centimeter. More preferably the apertures in the cleansing surface will occur at a frequency of from about 1.5 to 6 apertures per straight linear centimeter.

The apertures must at least be placed within the cleansing surface of the substrate element herein. Such apertures need not protrude completely through to the surface of the substrate which is opposite to the cleansing surface. When two or more plies or layers are used to form the water-insoluble substrate, apertures may or may not be placed in all of the plies or layers. Frequently, as noted more fully hereinafter, the substrate may comprise two layers one of which includes the cleansing surface and is apertured. The other layer or ply which forms a backing for the substrate with the cleansing surface is not apertured.

Apertures may be formed in the cleansing surface of the water-insoluble substrate as such a substrate, or layer thereof, is being formed or fabricated. Alternatively, apertures may be formed in the cleansing surface after the substrate, or ply or layer thereof, comprising the cleansing surface has been completely formed.

Nonwoven substrates made from synthetic materials useful in the present invention can be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 61 grams per square meter (gsm), available from Veratec, Inc., Walpole, Mass.; HEF 140-102, an apertured hydroentangled material containing about 50% rayon and 50% polyester, and having a basis weight of about 67 gsm, available from Veratec, Inc., Walpole, Mass.; Novonet® 149–616, a thermo-bonded grid patterned material containing about 100% polypropylene, and having a basis weight of about 60 gsm available from Veratec, Inc., Walpole, Mass.; Novonet® 149–801, a thermo-bonded grid patterned material containing about 69% rayon, about 25% polypropylene, and about 6% cotton, and having a basis weight of about 90 gsm, available from Veratec, Inc. Walpole, Mass.; Novonet® 149–191, a thermo-bonded grid patterned material containing about 69% rayon, about 25% polypropylene, and about 6% cotton, and having a basis weight of about 120 gsm, available from Veratec, Inc. Walpole, Mass; HEF Nubtex® 149–801, a nubbed, apertured hydroentangled material, containing about 100% polyester, and having a basis weight of about 84 gsm, available from Veratec, Inc. Walpole, Mass.; Keybak® 951V, a dry formed apertured material, containing about 75% rayon, about 25% acrylic fibers, and having a basis weight of about 51 gsm, available from Chicopee, New Brunswick, N.J.; Keybak® 1368, an apertured material, containing about 75% rayon, about 25% polyester, and having a basis weight of about 47 gsm, available from Chicopee, New Brunswick, N.J.; Duralace® 1236, an apertured, hydroentangled material, containing about 100% rayon, and having a basis weight from about 48 gsm to about 138 gsm, available from Chicopee, New Brunswick, N.J.; Duralace® 5904, an apertured, hydroentangled material, containing about 100% polyester, and having a basis weight from about 48 gsm to about 138 gsm, available from Chicopee, New Brunswick, N.J.; Chicopee® 5763, a carded hydroapertured material (8×6 apertures per inch, 3×2 apertures per cm), containing about 70% rayon, about 30% polyester, and a optionally a latex binder (Acrylate or EVA based) of up to about 5% w/w, and having a basis weight from about 60 gsm to about 90 gsm, available form Chicopee, New Brunswick, N.J.; Chicopee® 9900 series (e.g., Chicopee 9931, 62 gsm, 50/50 rayon/polyester, and Chicopee 9950 50 gsm, 50/50 rayon/polyester), a carded, hydroentangled material, containing a fiber composition of from 50% rayon/50% polyester to 0% rayon/100% polyester or 100% rayon/0% polyester, and having a basis weight of from about 36 gsm to about 84 gsm, available form Chicopee, New Brunswick, N.J.; Sontara 8868, a hydroentangled material, containing about 50% cellulose and about 50% polyester, and having a basis weight of about 72 gsm, available from Dupont Chemical Corp. Preferred nonwoven substrate materials have a basis weight of about from 24 gsm to about 96 gsm, more preferably from about 36 gsm to about 84 gsm, and most preferably from about 42 gsm to about 78 gsm.

The substrate can be made into a wide variety of shapes and forms including flat pads, thick pads, thin sheets, ball-shaped implements, irregularly shaped implements, and having sizes ranging from providing a cleansing surface area of at least about 5 cm$^2$. The exact size will depend upon the desired use and product characteristics. Especially convenient are square, circular, rectangular, or oval pads having a cleansing surface area of from about 6 cm$^2$ to 1000 cm$^2$, preferably from about 65 cm$^2$ to about 775 cm$^2$, and more preferably from about 150 cm$^2$ to about 400 Cm$^2$, and a thickness of from about 1 mil to about 500 mil, preferably from about 5 mil to about 250 mil, and more preferably from about 10 mil to about 100 mil.

Furthermore, it is desirable for the substrates of the present invention to have rounded corners. This feature prevents the tendency of water to accumulate at the corners of an unrounded rectangular, e.g., square, substrate. Corners, preferably all of the corners on the substrate, can be rounded to provide a radius of from about 1 to 4 cm. Preferably the rounded corners will have a radius of from about 2 to 3 cm.

The water insoluble substrates of the present invention can comprise one or more layers, each having different textures and abrasiveness. The differing textures can result from the use of different combinations of materials or from the use of different manufacturing processes or a combination thereof. A dual textured substrate can be made to provide the advantage of having a more abrasive side for exfoliation and a softer, absorbent side for gentle cleansing. In addition, separate layers of the substrate can be manufactured to have different colors, thereby helping the user to further distinguish the surfaces.

One especially preferred embodiment of the water-insoluble substrate is one wherein the substrate includes at least two layers or plies. The first layer is extensible when it is wetted and is preferably apertured. The second layer is less wet extensible when wetted than the first layer. Selected portions of the first layer are joined to the second layer to inhibit wet extension of the first layer in the plane of the first layer. When the first layer is wetted, the second layer constrains extension of the first layer in the plane of the first layer. As a result, portions of the first layer deform, such as by buckling or puckering, in the Z-direction (perpendicular to the plane of the first layer).

Figure 2:
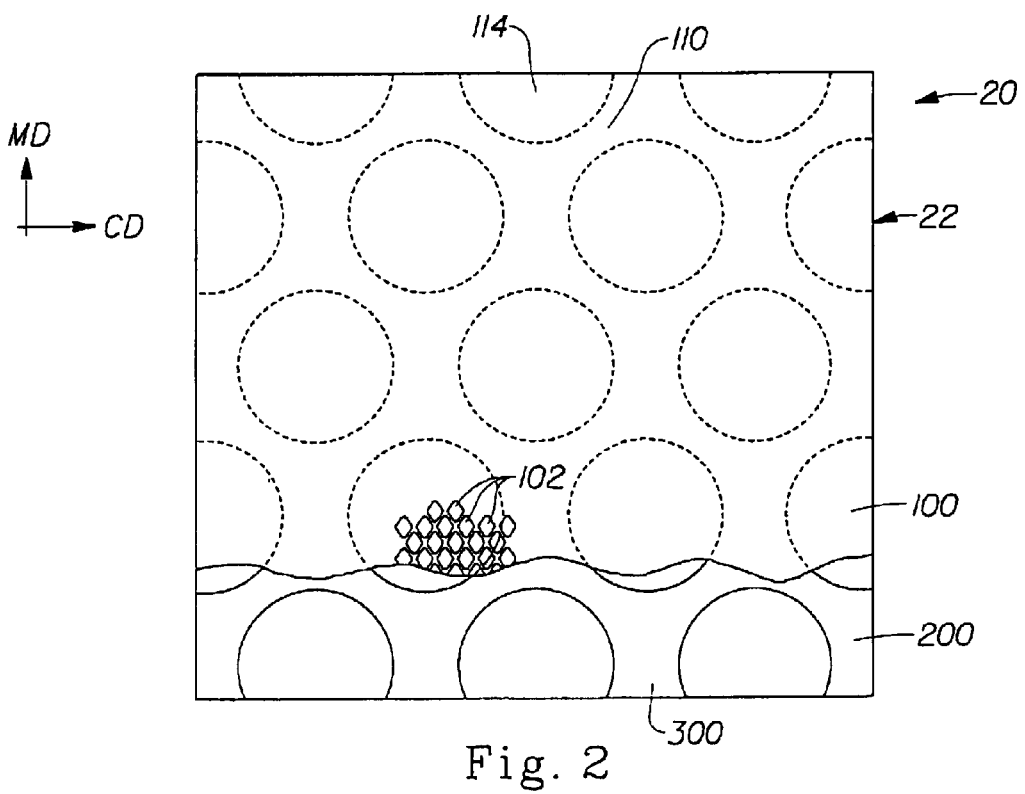
FIG. 2 is an illustration of another embodiment of a cleansing article of the present invention, the article including an extensible, apertured first layer and a less extensible second layer, with the first layer shown facing the viewer, and with a portion of the first layer shown cut away to show a continuous network of adhesive which serves to bond the first layer to the second layer, the bonded region defining generally circular-shaped unbonded regions.
Figure 3:
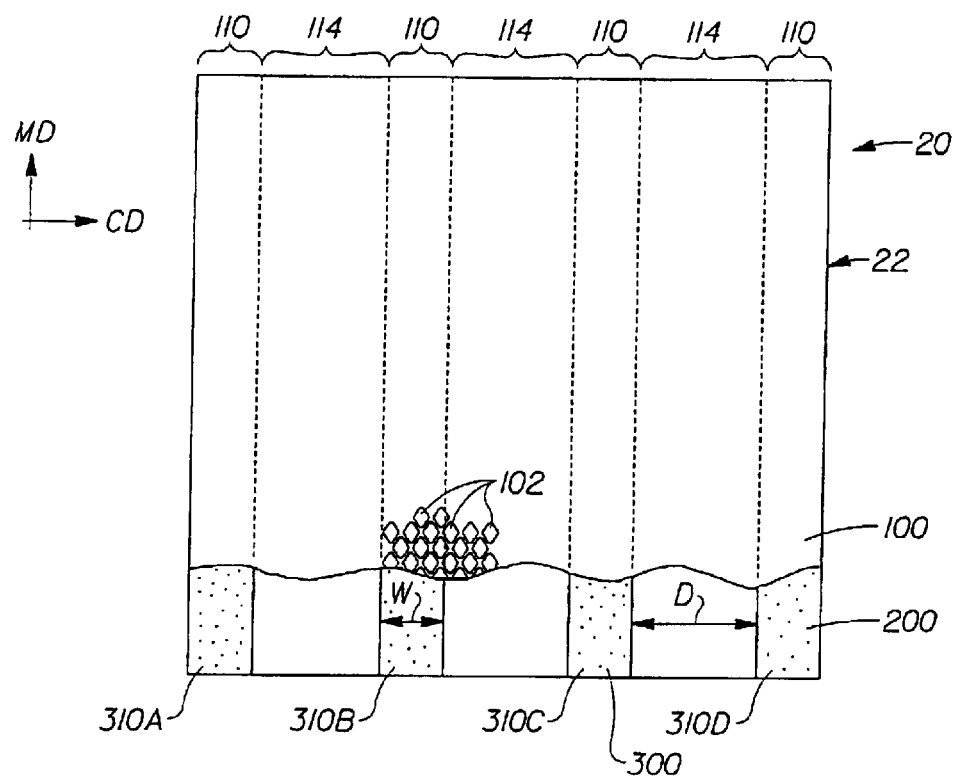
FIG. 3 is a plan view illustration of another embodiment of a cleansing article of the present invention, the article including an extensible, apertured first layer and a less extensible second layer, with the first layer shown facing the viewer, and with a portion of the apertured layer shown cut away to show generally parallel, spaced apart zones of adhesive extending generally parallel to the machine directions of the apertured layer and the non-apertured layer.

One embodiment of a water insoluble substrate having at least a portion that is wet extensible is illustrated in FIGS. 1–3 of the drawings. In this embodiment, the present invention comprises a multiple layer, i.e., two-ply, disposable wiping article 20. The disposable cleansing and conditioning article 20 comprises a substrate designated generally by reference numeral 22. The substrate 22 comprises a first layer 100 and a second layer 200. The first layer 100 is extensible, and in particular is extensible when wetted, e.g., the first layer is wet extensible. By "wet extensible" is meant that a material has a tendency to elongate in at least one direction when wetted. In general, "wetted" refers to wetting with aqueous solutions, such as water, which are capable of inducing extension in the first layer. For example, water relaxes the crepe in foreshortened paper, thereby causing an extension of the paper in at least one direction in the plane of the paper. Without being bound by theory, the relaxation of crepe may be a result of the loss of hydrogen bonds within the paper structure due to the presence of water. However, any fluid, mixture, or solution which could cause this crepe relaxation would be considered to "wet" the article. The second layer 200 is relatively less wet extensible when wetted than the first layer 100. Extensibility is measured according to the "Wet Extensibility Test" described below, and is reported as a percentage Selected portions of the first layer 100 are joined, directly or indirectly, to second layer 200 to inhibit wet extension of the first layer in the plane of the first layer. In FIGS. 1 and 2, selected portions of the first layer 100 are joined to the second layer 200 to provide continuous bonded regions designated 110 and discrete unbonded regions 114.

In a preferred embodiment shown in FIG. 1, the bonded regions 10 are shown as a continuous network of intersecting lines forming generally diamond-shaped unbonded regions 114. The width and spacing of the intersecting lines of bonded regions 110, may be adjusted to the desired size and spacing of the diamond-shaped unbonded regions 114. The continuous network of intersecting lines may be virtually any pattern, resulting in unbonded regions of virtually limitless geometric shapes, including, for example, squares, rectangles, and triangles. The network need not be completely continuous, nor limited to a pattern of straight or uniform lines, but may, for example, be a network resulting in circular, oval, or other non-polygonal geometric shapes. An adhesive, such as a hot melt adhesive, designated by reference numeral 300 in FIGS. 1–3, can be used to join the first layer 100 to second layer 200.

When the first layer is wetted, there is a tendency for the first layer 100 to expand along one or more directions in the plane of the first layer. (The plane of the first layer is parallel to the plane of FIG. 1). However, because of the relatively lower wet extensibility of the second layer 200, the second layer constrains extension of the first layer 100 in the plane of the first layer. As a result, the unbonded regions 114 of the first layer 100 deform, such as by buckling or puckering in the Z-direction, perpendicular to the plane of the first layer 100.

Figure 5A:
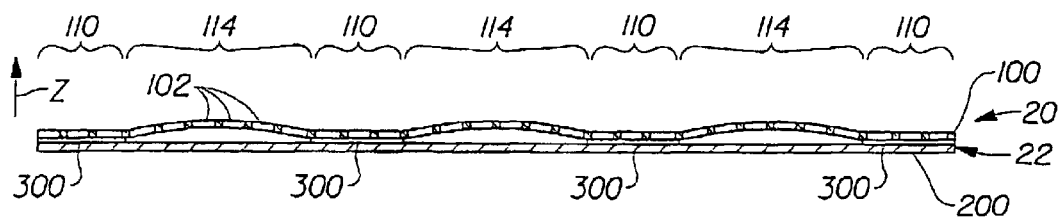
FIG. 5A is a cross-sectional illustration of the cleansing article of the present invention taken along the direction indicated by line 5—5 in FIG. 1, and showing the article prior to wetting of the apertured first layer.
Figure 5B:
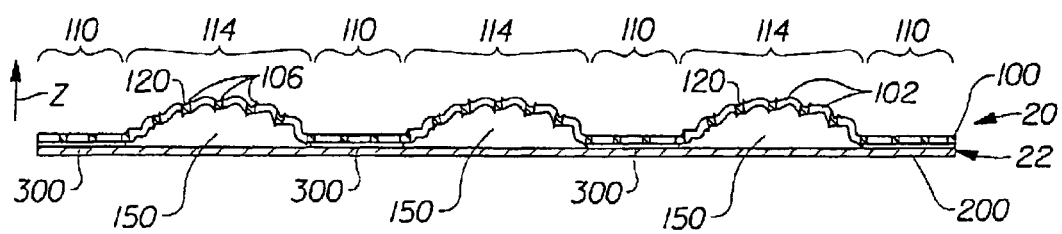
FIG. 5B is a cross-sectional illustration taken along the direction indicated by line 5—5 in FIG. 1, and showing the article after wetting of the apertured first layer.

FIG. 5A is a cross-sectional illustration of the cleansing and conditioning article 20 prior to wetting of the first layer 100. As shown in FIG. 5A, the wiping article is generally flat prior to wetting. FIG. 5B is a cross-sectional illustration similar to that of FIG. 5A, but showing the article 20 after wetting of the first layer 100. FIG. 5B shows out of plane deformation of the first layer 100 upon wetting of the first layer 100. The Z-direction is indicated in FIGS. 5A and 5B. The deformation of the wetted first layer 100 provides the article 20 with elevated ridges 120 which increase the wet texture, wet caliper (thickness) and wet bulk of the article 20. The elevated ridges 120 also provide pockets 150 disposed between the unbonded portions of the first layer 100 and the underlying portions of the second layer. In particular, the article 20 has a wet caliper to dry caliper ratio which is greater than 1.0, preferably at least about 1.1, more preferably at least about 1.2, and most preferably at least about 1.4. The wet caliper to dry caliper ratio is a measure of the thickness of the article 20, when wetted, relative to the thickness of the dry article 20 prior to wetting. The wet caliper to dry caliper ratio is measured according to the procedure "Wet Caliper to Dry Caliper Ratio" provided hereinafter.

In the preferred embodiment shown in FIG. 1, the first layer 100 is apertured, the first layer 100 comprising a plurality of apertures 102 which extend through the thickness of the first layer 100. Apertures add greatly to the desired texture and bulk of wiping article 20. In FIGS. 1–3, apertures 102 are shown on only a portion of the first layer 100 for clarity. When an apertured first layer is used, the deformation of the wetted first layer 100 again provides the article 100 with elevated ridges 120 which increase the wet texture, wet caliper (thickness) and wet bulk of the article 20. However, in this embodiment, the elevated ridges 120 have apertures 102 which provide a flow path through which liquids and/or small particles can enter the pockets 150.

Additionally, since the article 20, or alternate single ply apertured substrate, is used with, or includes a lathering agent, such as a surfactant, the apertures 102 can aid in the incorporation of air during the lathering process, thereby improving lather generation. For instance, a portion of the article 20 can be coated with or otherwise treated with a surfactant composition, as described more fully below. The article 20 can be wetted with water to activate the surfactant, and the airflow generated through the apertures 102 during use of the article (e.g. washing or wiping) can help to generate lather.

The size and number of the apertures 102 can influence the speed of lather generation and the quality of lather produced. A relatively small number of relatively large apertures 102 will tend to reduce the time required to generate lather, but will yield relatively large lather bubbles with a translucent appearance. On the other hand, a relatively larger number of relatively smaller apertures 102 will tend to reduce bubble size, thereby increasing lather creaminess and opacity, but at the expense of increasing the time required to generate lather.

Another advantage has been identified when first layer 100 is apertured. As shown in FIG. 5B, in addition to the formation of elevated ridges 120, the wet extension of first layer 100 around apertures 102 forms what can best be described as cusps 106, or surface irregularities formed by the apertures 102. Cusps 106 give added texture to the surface on the side of apertured surface 22 of first layer 100. This added texture may be modified as needed by adjusting the size and spacing of apertures 102.

Also depicted in FIG. 3, is another variation on the configuration of bonded and unbonded regions. In the embodiment shown, the bonded regions 110 are generally parallel, spaced apart regions which extend along substantially the full length of the article 20, and define generally parallel, spaced apart unbonded regions 114 of the first layer 100. In FIG. 3, the unbonded regions 114 extend along substantially the full length of the article 20. An adhesive, designated by reference numeral 300 in FIGS. 1 and 2 and numerals 300, 310A–310D in FIG. 3, can be used to join the first layer 100 to the second layer 200.

In a preferred embodiment, a wipe 20 of the present invention comprises an apertured cellulosic paper first layer bonded to a synthetic nonwoven in a continuous network of intersecting lines defining diamond-shaped unbonded regions. This combination of materials and bonding method and pattern provides for a preferred wipe that exhibits increased texture and bulk on one side upon wetting, while maintaining relatively smooth softness on the other side, and has a wet caliper greater than the dry caliper.

In addition to the above description, it has been found that an additional processing step involving heating the substrate after bonding can be used to further improve texture and bulk, as well as the general aesthetic qualities of the wipe. Without being bound by theory, it is believed that the process of heating causes the thermoplastic adhesive to contract, thereby further causing out-of-plane (Z-direction) deformation of the first layer, as well as the second layer. By contracting in the plane of the wipe article, both layers experience a Z-direction increase in caliper, giving increased overall caliper with a pleasing quilted look.

For example, a wipe that has been adhesively bonded with an EVA hot melt adhesive (one suitable adhesive is a hot melt adhesive commercially available as H1382-01 from Ato-Findley Adhesives of Wauwatosa, Wis.), may increase in caliper between 10–20% after a post-lamination heat treatment. In this case, a suitable hot melt adhesive is applied and the resulting article is cooled to room temperature. Heat treatment may then be performed, for example, raising the temperature to 100 degrees Celsius for 20 seconds is sufficient to initiate contraction of the polymer network. While not being bound by theory, it is believed that for this process to be effective, the pattern of bonding must be a continuous or essentially continuous network. Discrete bond sites may not sufficiently contract to improve the appearance of the article.

First Layer:

Referring to the components of the article 20 in more detail, suitable materials from which the first layer 100 can be formed include foreshortened (such as by creping) wet-laid paper webs. Other suitable materials can include woven materials, nonwoven materials, foams, battings, and the like.

The first layer 100 should be constructed to have a wet extensibility of at least 4 percent, more preferably at least about 10 percent, and still more preferably at least about 20 percent. In one embodiment, the first layer has a wet extensibility of at least about 25 percent. Preferably, the difference between the wet extensibility of the first layer and the wet extensibility of the second layer (the wet extensibility of the second layer subtracted from the wet extensibility of the first layer) is at least about 4 percent, more preferably at least about 10 percent, and still more preferably at least about 25 percent.

The fibers or filaments of the first layer 100 can be natural (e.g. cellulosic fibers such as wood pulp fibers, cotton linters, and bagasse fibers) or synthetic (e.g. polyolefins, rayon, polyamides or polyesters), or combinations thereof.

Figure 4:
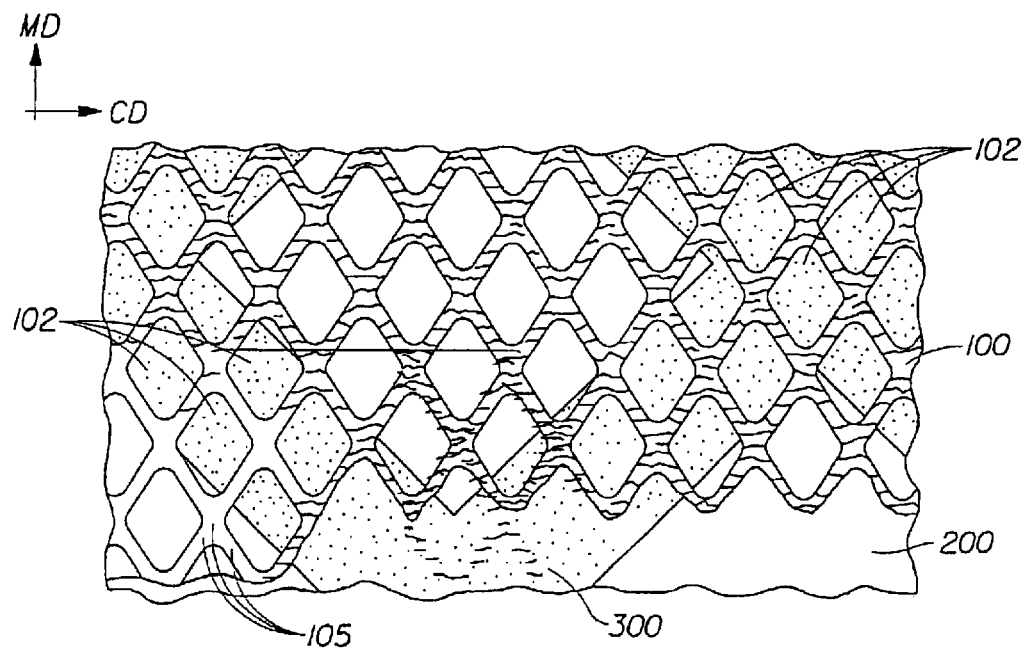
FIG. 4 is an illustration of a portion of the cleansing article shown in FIG. 1, FIG. 4 being enlarged relative to FIG. 1 to illustrate the apertures in the extensible first layer and creping ridges in the apertured layer.

In another preferred embodiment, the first layer 100 comprises a wetlaid paper web of cellulosic wood pulp fibers which is foreshortened at least about 4 percent, more preferably at least about 10 percent, and still more preferably at least about 20 percent, by dry creping. Referring to FIG. 4, the first layer 100 is shown comprising crepe ridges 105 corresponding to the foreshortening of the first layer 100. The machine direction (MD) and cross machine direction (CD) are indicated in FIGS. 1–4. The machine direction corresponds to the direction of manufacture of the paper web of first layer 100. The crepe ridges 105 are generally perpendicular to the machine direction, and generally parallel to the cross machine direction of the paper web of first layer 100.

The paper web of the first layer 100 can have a basis weight of between about 15 to about 65 grams per square meter. In a preferred embodiment, the basis weight of the first layer is between about 25 to about 45 grams per square meter, and in a more preferred embodiment, the basis weight of the first layer 100 is about 35 grams per square meter.

It is believed that the paper strength can significantly alter the overall appearance of the complete article. The amount of crepe input to the first layer is directly proportional to the amount of planar expansion and thereby the amount of caliper generated upon wetting. However, if the wet strength of the paper article is insufficient, the "buckles" may collapse to form a more "wrinkled" product having less caliper. Therefore both crepe and wet strength can be adjusted to provide an amount of texture based on the intended use of the article. Wet burst measurements can be made with a Thwing-Albert Burst Tester model number 1300-77, which tests peak load of a fully wetted substrate. The test utilizes a 1.3 cm ball diameter, a 12.7 cm/min ball velocity, and clamps the test sample around a 8.9 cm diameter circle perpendicular to the motion of the ball. Peak load wet burst strengths are between 100 and 1200 grams per ply. More preferably between 400 and 700 grams per ply and most preferably between 500 and 600 grams per ply.

In a more preferred embodiment, the first layer 100 comprises an apertured wetlaid paper web of cellulosic wood pulp fibers. The apertures 102 can be formed in the first layer 100 in any suitable manner. For instance, the apertures 102 can be formed in the first layer 100 during formation of the paper web of the first layer 100, or alternatively, after the paper web of the first layer 100 is manufactured. In one embodiment, the paper web of the first layer 100 is produced according to the teachings of one or more of the following U.S. patents, which patents are incorporated herein by reference: U.S. Pat. No. 5,245,025 issued Sept. 14, 1993 to Trokhan et al.; U.S. Pat. No. 5,277,761 issued Jan. 11, 1994 to Phan et al.; and U.S. Pat. No. 5,654,076 issued Aug. 5, 1997 to Trokhan et al. In particular, U.S. Pat. No. 5,277,761 at Column 10 discloses formation of a paper web having apertures.

Prior to wetting of the first layer, the creped first layer 100 can have between about 0.5 and 50 apertures per square centimeter, and more preferably between about 0.5 and 16 apertures per square centimeter. Wetting a creped paper web causes the web, if unrestrained, to expand in at least one direction, such as the machine direction, so that the number of apertures 102 per square area after wetting can be smaller than the number of apertures per square area prior to wetting. Similarly, when apertures are formed in a paper web, and the paper web is subsequently creped, the number of apertures per square area prior to creping will be smaller than the number of apertures per square area after creping. Accordingly references to paper web dimensions refer to dimensions after creping and prior to wetting.

The apertures 102 can comprise between about 15 and about 75 percent of the total surface of the first layer 100. The apertures 102 shown in FIG. 2 are bilaterally staggered (staggered in both the machine and cross machine directions) in a repeating, nonrandom pattern. In one embodiment, the first layer 100 comprises a paper web which is dry creped 25 percent (25 percent foreshortening) with greater than about 25 percent wet extensibility, and has about 6 to 8 apertures, 102, per square centimeter, the apertures 102 having a length 103 (FIG. 4) of about 0.25 to 0.46 centimeters and a width 104 of about 0.17 to 0.38 centimeter, and a distance between apertures 106 of about 0.12 to to about 0.20 centimeter.

The paper web is manufactured by first forming an aqueous papermaking furnish. The furnish comprises papermaking fibers, and can further comprise various additives. U.S. Pat. No. 5,223,096 issued Jun. 29, 1993 to Phan et al. is incorporated herein by reference for the purpose of disclosing various wood pulps and papermaking additives.

A suitable paper web for making the first layer 100 can be manufactured according to the following description. A papermaking furnish is prepared from water and highly refined Kraft pulp derived from northern softwoods (NSK), the paper furnish having a fiber consistency of about 0.2 percent (dry fiber weight divided by the total weight of the furnish equals 0.002). A dry strength additive such as carboxymethyl cellulose (CMC) is added to the 100% NSK furnish in the amount of about 5 pounds of CMC solids per ton of dry papermaking fibers. A wet strength additive such as Kymene 557H (available from Hercules, Inc. of Wilmington, Del.) is added to the furnish in the amount of about 28 pounds of Kymene solids per ton of dry papermaking fibers.

Figure 6:
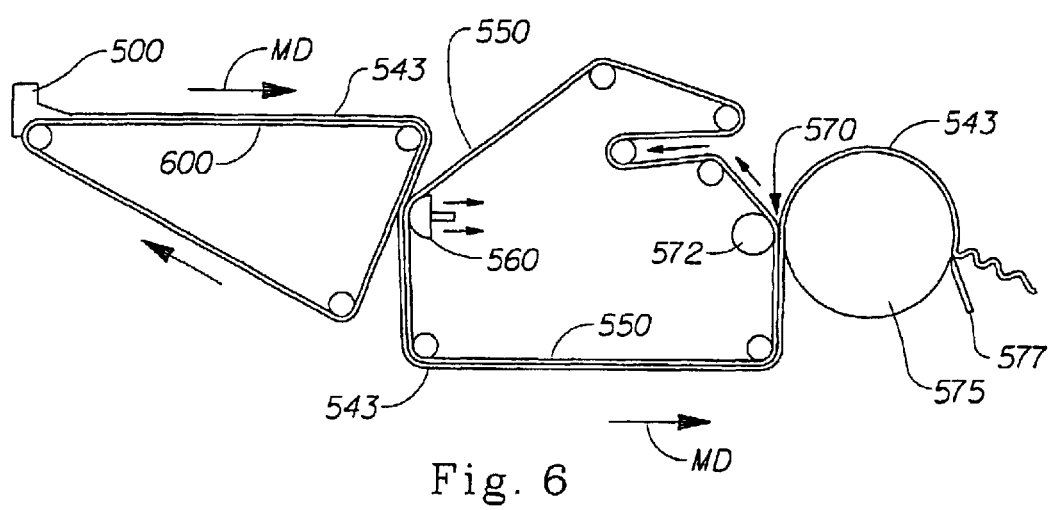
FIG. 6 is an illustration of a paper machine which can be used to make cellulosic paper webs that can be used in forming the apertured substrate portion of the cleansing articles herein.

Referring to FIG. 6, the furnish is deposited from a headbox 500 of a papermaking machine to a forming element 600 at a fiber consistency of about 0.2 percent. The forming element 600 is in the form of a continuous belt in FIG. 6. The slurry of papermaking fibers is deposited on the forming element 600, and water is drained from the slurry through the forming element 600 to form an embryonic web of papermaking fibers designated by reference numeral 543 in FIG. 6.

Figure 7:
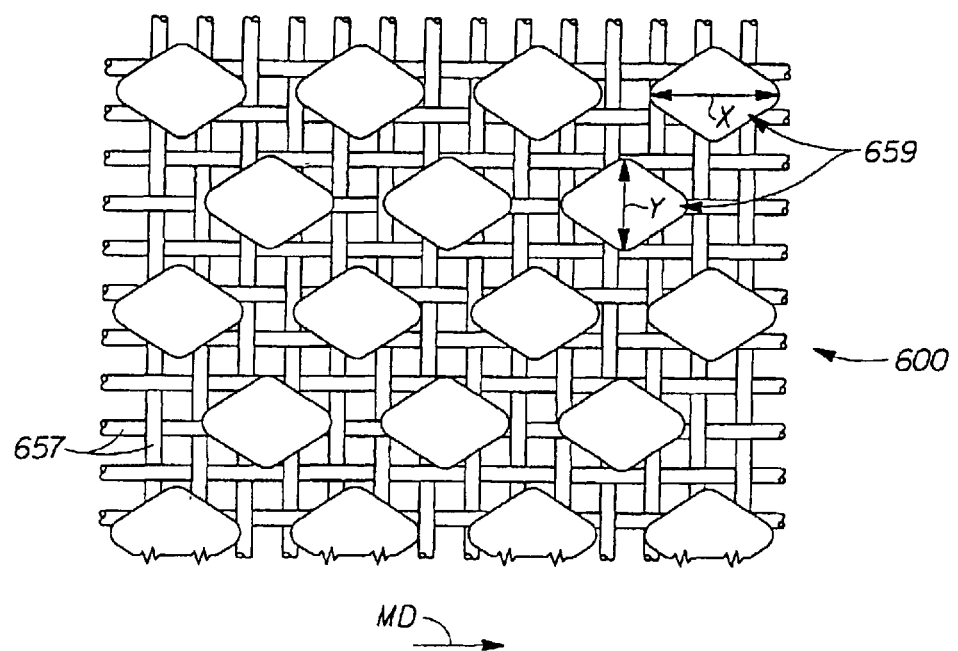
FIG. 7 is an illustration of a forming element which can be used to manufacture a cellulosic paper web with apertures that can be employed in the articles herein.

FIG. 7 shows a portion of the forming element 600. The forming element 600 has two mutually opposed faces. The face which is shown in FIG. 7 is the face which contacts the papermaking fibers of the web being formed. A description of a forming element of the type shown in FIG. 7 is provided in the above referenced U.S. Pat. Nos. 5,245,025; 5,277,761; and 5,654,076.

The forming element 600 has flow restriction members in the form of resin protuberances 659. The forming element 600 shown comprises a patterned array of protuberances 659 joined to a reinforcing structure 657, which may comprise a foraminous element, such as a woven screen or other apertured framework. The protuberances 659 extend above the reinforcing structure 657.

A suitable forming element 600 has about 6 protuberances 659 per square centimeter of surface of the forming element 600, with the protuberances 659 covering about 35 percent of the surface of the forming element 600, as viewed in FIG. 7, and the protuberances extending 0.065 centimeter above the surface of the reinforcing structure 657. The protuberances can have a machine direction length X of about 0.384 centimeter and a cross machine direction width Y of about 0.234 centimeter.

The reinforcing structure 657 is substantially fluid pervious, while the protuberances 659 are substantially fluid impervious. Accordingly, as the liquid in the papermaking furnish drains through the forming element, the papermaking fibers in the furnish will be retained on the reinforcing structure 657, leaving apertures in the embryonic web 543 corresponding generally in size, shape and location to the size, shape and location of the protuberances 659.

Referring back to FIG. 6, the embryonic web 543 is transferred to a conventional dewatering felt 550 with the aid of a vacuum pick up shoe 560. The web 543 is transferred to the felt 550 at a fiber consistency of about 4 percent. The web 543 is carried on the felt 550 to a nip 570 formed between a vacuum pressure roll 572 and a Yankee dryer drum 575. The web 543 is dried on the Yankee drum 575 to a fiber consistency of about 96 percent, at which point the web is creped from the Yankee drum 575 with a doctor blade 577 having a bevel angle of about 25 degrees and an impact angle of about 81 degrees. The web is wound on a reel at a rate (lineal feet per second) which is 25 percent slower than the surface speed of the Yankee drum (reel speed equals 0.75 times the Yankee speed) to foreshorten the web about 25 percent. The foreshortened web can have a basis weight of about 33 grams per square meter, and a thickness of about 12 to 13 mils (0.012 to 0.013 inch) as measured with a confining pressure of 95 grams per square inch and a load foot having a diameter of 5 centimeters. The resulting foreshortened web can be used to form a first layer 100 having a wet extensibility of at least about 25 percent.

Second Layer:

The first layer 100 is joined to the second layer 200 to constrain extension of selected portions of the first layer 100 when the first layer is wetted. The second layer 200 has a lower wet extensibility than that of the first layer 100.

Ply Bonding:

Selected portions of the first layer 100 can be joined directly (or indirectly such as through a third component) to the second layer 200 in a predetermined bonding pattern to provide a plurality of bonded and unbonded regions of the first layer 100. In FIGS. 1–3, the bonded regions are designated 110, and the unbonded regions are designated 114. Each of the first and second layers 100 and 200 can have a machine direction, and the first and second layers can be bonded so that the machine direction of the first layer is generally parallel to the machine direction of the second layer.

The first layer 100 and the second layer 200 can be joined using any suitable method, including but not limited to adhesive bonding, mechanical bonding, thermal bonding, mechanical-thermal bonding, ultrasonic bonding, and combinations thereof. In particular, in a preferred embodiment, adhesive is applied by printing methods, such as gravure printing, reverse gravure printing, screen printing, flexographic printing, and the like. In one preferred embodiment, EVA hot melt adhesive may be screen printed in a lattice pattern generally as shown in FIG. 1. The suitable screen for this embodiment is a 40 mesh Galvano screen manufactured by Rothtec Engraving Corp., New Bedford, Mass.

The adhesive is preferably water insoluble so that the article 20 can be wetted with water without delamination of the first and second layers. The adhesive is preferably also surfactant tolerant. By "surfactant tolerant" it is meant that the bonding characteristics of the adhesive are not degraded by the presence of surfactants. Suitable adhesives include EVA (ethylene vinyl acetate) based hot melt adhesives. One suitable adhesive is a hot melt adhesive commercially available as H1382-01 from Ato-Findley Adhesives of Wauwatosa, Wis.

With reference to FIGS. 1 and 2, the hot melt adhesive can be applied to the nonwoven second layer 200 in a continuous network defining a discontinuous plurality of unbonded regions 114. In one preferred embodiment, as shown in FIG. 1, the adhesive is applied as parallel, spaced apart lines in a first direction, intersected by parallel, spaced apart lines in a second direction. The intersecting lines form diamond-shaped patterns of unbonded regions in the final wipe. In the embodiment shown in FIG. 1, the hot melt adhesive can be applied in lines having a width of about 0.025 centimeter to about 1.25 centimeter, preferably about 0.125 to about 0.18 centimeter. The spacing between adjacent lines of adhesive can be about 0.5 to 5.0 centimeter, preferably about 1.0 to 1.5 centimeter.

With reference to FIG. 3, the hot melt adhesive can be applied to the nonwoven second layer 200 in bands which extend generally parallel to the machine direction of the nonwoven second layer 200. The hot melt adhesive can be applied in stripes 310 having a width W (FIG. 3) of about 0.32 centimeter to 2.54 centimeters. The spacing D between adjacent adhesive stripes can be about 0.32 centimeter to 5.1 centimeters. In FIG. 3, four stripes 310A, 310B, 310C, and 310D are shown.

When applied as parallel stripes, lines, or bands, the adhesive can be applied to the nonwoven second layer 200 using a slot coating applicator. A suitable slot coating applicator is a Nordson MX series hot melter with extrusion head commercially available from the Nordson Company of Norcross, Ga. The H1382-01 adhesive referenced above can be applied to the second layer 200 at a temperature of about 350 Fahrenheit, at an application level of about 0.03 grams of adhesive per square inch. Immediately following application of the adhesive to the nonwoven second layer 200, the nonwoven second layer 200 and the paper first layer 100 can be bonded together by pressing the two layers 100 and 200 together with the adhesive disposed between the second layer 200 and the first layer 100. One suitable means for pressing the two layers 100 and 200 together is by passing the two layers through a nip formed between two rollers, with the rollers loaded to provide adequate nip pressure for bonding.

The resulting laminate of the first and second layers can have an average dry caliper of about 28.5 mils (0.072 centimeter), an average wet caliper of about 32.1 mils (0.082 centimeter), and a wet caliper to dry caliper ratio of about 1.1. The dry caliper, wet caliper, and wet caliper to dry caliper ratio are measured as described below under "Wet Caliper to Dry Caliper Ratio."

Wet Extensiblity Test

The wet extensibility of a layer, such as the layer 100 or the layer 200, is determined using the following procedure. Samples are conditioned at 70 degrees Fahrenheit and 50 percent relative humidity for two hours prior to testing.

First, the direction of greatest wet extensibility in the plane of the layer is determined. For dry creped paper webs, this direction will be parallel to the machine direction, and generally perpendicular to the crepe ridges.

If the direction of greatest wet extensibility is not known, the direction can be determined by cutting seven samples from a sheet with sample lengths oriented between 0 degrees and 90 degrees, inclusive, with respect to a reference line drawn on the sheet. The samples are then measured as set forth below to determine the direction of greatest wet extensibility.

Once the direction of the greatest wet extensibility is determined, 8 samples are cut to have a length of about 18 centimeters measured parallel to the direction of greatest wet extensibility, and a width of at least 2.54 centimeters. The samples are cut from unbonded portions of the layers 100 and 200, or, if unbonded portions having the above dimensions cannot be cut from the article 20, then samples are cut from the layers 100 and 200 prior to bonding the layers together. Two marks are placed on each sample, such as with an ink pen. The marks are spaced apart 12.7 centimeters as measured parallel to the direction of greatest wet extensibility. This 12.7 centimeter length is the initial dry test length of the sample.

Each sample is thoroughly wetted by submerging the sample in distilled water for 30 seconds in a water bath. Each sample is removed from the water bath and immediately supported to hang vertically so that a line through the two marks is generally vertical. The wet sample is supported such that the support does not interfere with extension between the two marks (e.g. with a clip which does not contact the sample between the two marks). The wet test length of the sample is the distance between the two marks. The distance is measured within 30 seconds of removing the sample from the water bath.

For each sample, the percent wet extension is calculated as

Sample Wet Extension=(wet test length−initial dry test length)/(initial dry test length)×100

For example, for a measured wet test length of 16.5 centimeters and an initial dry test length of 12.7 centimeters, the wet extension is ((16.5−12.7)/12.7)×100=30 percent. The wet extensibility of the samples is the average of 8 calculated values of sample wet extension.

In the preferred embodiment of the invention herein, the first layer preferably has a wet extensibility of at least about 4 percent, more preferably at least about 10 percent, and still more preferably at least about 20 percent as measured using the "Wet Extensibility Test" provided hereinbefore. The first layer can be foreshortened to provide the desired wet extensibility. In one embodiment, the first layer comprises a wet laid, apertured paper web which is foreshortened about 30 percent by dry creping. The second layer has a wet extensibility that is less than that of the first layer. The wet extensibility of the first layer minus the wet extensibility of the second layer is preferably at least about 4 percent, more preferably at least about 10 percent, and still more preferably at least about 20 percent.

Wet Caliper to Dry Caliper Ratio

The wet caliper to dry caliper ratio is measured using a Thwing-Albert Instrument Co. Electronic Thickness Tester Model II, using the following procedure. Samples are conditioned at 70 degrees Fahrenheit and 50 percent relative humidity for two hours prior to testing.

The dry caliper of the article 20 is measured using a confining pressure of 95 grams per square inch and a load foot having a diameter of 2 inches. The dry caliper is measured for eight samples. For each sample, the caliper is measured with the load foot centered on an unbonded region of the first layer 100. The eight caliper measurements are averaged to provide an average dry caliper.

Each sample is then wetted by submerging the sample in a distilled water bath for 30 seconds. The sample is then removed from the water bath and drained by hanging vertically for about five seconds. The caliper of the wet sample is measured within 30 seconds of removing the sample from the bath. The wet caliper is measured in the same location in which the dry caliper was previously measured. The eight wet caliper measurements are averaged to provide an average wet caliper. The wet caliper to dry caliper ratio is the average wet caliper divided by the average dry caliper.

The wet caliper to dry caliper ratio is the average wet caliper divided by the average dry caliper.

In the preferred two-ply substrate herein, the disposable cleansing and conditioning article can have a wet caliper to dry caliper ratio greater than 1.0, more preferably at least about 1.1, even more preferably at least about 1.2, and most preferably at least about 1.4.

Lathering Surfactant

Besides the water-insoluble substrate, the articles of the present invention also comprise one or more lathering surfactants which are releasably associated with the water-insoluble substrate. Thus the lathering surfactants can be added onto or impregnated into the substrate. Generally this will be done prior to the point of use of the article, i.e., the surfactants will be combined with the article and the article dried before the article is ultimately wetted for use. Preferred articles of the present invention comprise a sufficient amount of one or more lathering surfactants such that the articles are capable of generating ≧30 ml of Lather Volume (medium hardness water at 95° C.) according to the Lather Volume Test described below.

Generally the articles will contain from about 0.5% to 250%, by weight of the substrate, of a lathering surfactant that is releasably associated with the substrate. Preferably, the articles of the present invention comprise from about 0.5% to about 12.5%, more preferably from about 0.75% to about 11%, and most preferably from about 1% to about 10%, based on the weight of the water insoluble substrate, of a lathering surfactant component.

By a lathering surfactant is meant a surfactant, which when combined with water and mechanically agitated generates a foam or lather sufficient to cause the article, as a whole, to provide a lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lather surfactants, amphoteric lathering surfactants, and mixtures thereof. Generally, the lathering surfactants do not strongly interfere with deposition of any conditioning agents that are present, e.g., are fairly water soluble, and usually have an HLB value of above 10. Cationic surfactants can also be used as optional components, provided they do not negatively impact the overall lathering characteristics of the required lathering surfactants.

Anionic Lathering Surfactants

Nonlimiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975, all of which are incorporated by reference herein in their entirety.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulas $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R1-SO_3-M$$ 

wherein R1 is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between $C_8$ and $C_{16}$. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. $C_{8-30}$ alcohols, with sugars or starches or sugar or starch polymers, i.e., glycosides or polyglycosides. These compounds can be represented by the formula $(S)_n—O—R$ wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R^1R^2R^3NO$, wherein $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of $C_8$–$C_{14}$ glucose amides, $C_8$–$C_{14}$ alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl di-methyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

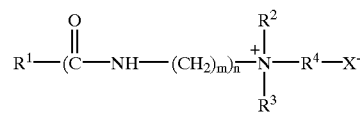

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl Dimethyl Betaine (this Material also has the CTFA Designation Cetyl Betaine)

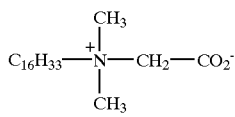

Cocamidopropylbetaine

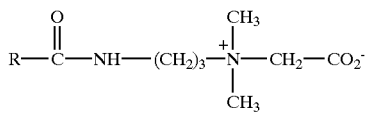

wherein R has from about 9 to about 13 carbon atoms
Cocamidopropyl Hydroxy Sultaine

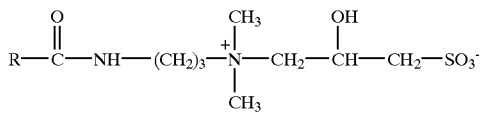

wherein R has from about 9 to about 13 carbon atoms,

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Lather Volume Test

The articles of the present invention preferably comprise enough of the lathering surfactant such that the articles are capable of generating greater than or equal to about 30 ml, more preferably greater than or equal to about 50 ml, even more preferably greater than or equal to about 75 ml, and most preferably greater than or equal to about 150 ml of Average Lather Volume. The Average Lather Volume is a measurement determined by the Lather Volume Test. This test provides a consistent measurement of the volume of lather/foam generated by the articles described herein. The Lather Volume Test protocol is described as follows:

(1) Hands are washed with Ivory bar before conducting the test. This step removes any soils which may affect the accuracy of the measurement.

(2) The test article is held open in the non-dominant hand with the edges turned up.

(3) 10 m. of water (medium hardness of about 8–10 grains per gallon) at 95° C. is added onto the test article via a 10 cc syringe or a Brinkmann repipetter.

(4) The lather is then generated by rubbing the test article with the dominant hand in a circular motion between the palms for 6 seconds (~2 rotations per second), using moderate pressure (e.g., 4 oz.), and allowing the article to ball-up between the palms of the hand.

(5) The test article is then held open in the non-dominant hand and an additional 10 ml of water (medium hardness of about 8–10 grains per gallon) at 95° C. is added onto the test article via a 10 cc syringe or a Brinkmann repipetter. The wetted article is again rubbed with the dominant had (3 rotations) using moderate force (e.g, 4 oz.) so that the test article becomes balled-up between the palms.

(6) The test article is then opened and rubbed 5 times by holding one edge of the article in one hand and rotating the hand holding the other side to further activate lather.

(7) The test article is then flipped over and Step #6 is repeated using the other hand.

(8) The lather is gathered by holding the test article in a cupped hand and scraping the lather off the test article with the other hand, being careful to only scrape lather from the test article. The lather from the test article is placed into a graduated cylinder or beaker big enough to hold the generated lather. This procedure is repeated 5 times on the same test article, and the lather from each iteration is accumulated in the same graduated cylinder or beaker. The total accumulated lather from these iterations is designated as the Lather Volume.

(9) To achieve consistent results, the Average Lather Volume is reported as the average of three test sample replications of Steps 1–8.

Conditioning Component

The articles of the present invention will preferably further comprise a conditioning component which is useful for providing a conditioning benefit to the skin or hair during the use of the article. The conditioning component can comprise from about 0.05% to about 99%, preferably from about 0.1% to about 50%, and more preferably from about 1% to about 25% by weight of said water insoluble substrate.

The conditioning component useful in the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e. greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$=the sum of the heat of vaporization additive group contributions, and $\sum_i m_i$=the sum of the molar volume additive group contributions Standard tabulations of heat of vaporization and molar volume additive group contributions for a wide variety of atoms and groups of atoms are collected in Barton, A. F. M. Handbook of Solubility Parameters, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", Polymer Engineering and Science, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, Handbook of Chemistry and Physics, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the Handbook of Solubility Parameters are reported in units of kJ/mol. However, these tabulated heat of vaporization values are readily converted to cal/mol using the following well-known relationships:

1 $J/mol$=0.239006 $cal/mol$ and 1000 $J$=1 $kJ$.

See Gordon, A. J. et al., The Chemist's Companion, John Wiley & Sons, pp. 456–463, (1972), which is incorporated by reference herein in its entirety.

Solubility parameters have also been tabulated for a wide variety of chemical materials. Tabulations of solubility parameters are found in the above-cited Handbook of Solubility Parameters. Also, see "Solubility Effects In Product, Package, Penetration, And Preservation", C. D. Vaughan, Cosmetics and Toiletries, vol. 103, October 1988, pp. 47–69, which is incorporated by reference herein in its entirety.

Nonlimiting examples of conditioning agents useful as oil soluble conditioning agents include those selected from the group consisting of mineral oil, petrolatum, $C_7$–$C_{40}$ branched chain hydrocarbons, $C_1$–$C_{30}$ alcohol esters of $C_1$–$C_{30}$ carboxylic acids, $C_1$–$C_{30}$ alcohol esters of $C_2$–$C_{30}$ dicarboxylic acids, monoglycerides of $C_1$–$C_{30}$ carboxylic acids, diglycerides of $C_1$–$C_{30}$ carboxylic acids, triglycerides of $C_1$–$C_{30}$ carboxylic acids, ethylene glycol monoesters of $C_1$–$C_{30}$ carboxylic acids, ethylene glycol diesters of $C_1$–$C_{30}$ carboxylic acids, propylene glycol monoesters of $C_1$–$C_{30}$ carboxylic acids, propylene glycol diesters of $C_1$–$C_{30}$ carboxylic acids, $C_1$–$C_{30}$ carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol $C_4$–$C_{20}$ alkyl ethers, di $C_8$–$C_{30}$ alkyl ethers, and mixtures thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the $C_7$–$C_{40}$ isoparaffins, which are $C_7$–$C_{40}$ branched hydrocarbons.

Also useful are $C_1$–$C_{30}$ alcohol esters of $C_1$–$C_{30}$ carboxylic acids and of $C_2$–$C_{30}$ dicarboxylic acids, including straight and branched chain materials as well as aromatic derivatives. Also useful are esters such as monoglycerides of $C_1$–$C_{30}$ carboxylic acids, diglycerides of $C_1$–$C_{30}$ carboxylic acids, triglycerides of $C_1$–$C_{30}$ carboxylic acids, ethylene glycol monoesters of $C_1$–$C_{30}$ carboxylic acids, ethylene glycol diesters of $C_1$–$C_{30}$ carboxylic acids, propylene glycol monoesters of $C_1$–$C_{30}$ carboxylic acids, and propylene glycol diesters of $C_1$–$C_{30}$ carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various $C_1$–$C_{30}$ monoesters and polyesters of glycerin and related materials. These esters are derived from glycerin and one or more carboxylic acid moieties. Depending on the constituent acid and glycerin, these esters can be in either liquid or solid form at room temperature. Nonlimiting examples of solid esters include: glyceryl tribehenate, glyceryl stearate, glyceryl palmitate, glyceryl distearate, glyceryl dipalmitate.

Also useful are various $C_1$–$C_{30}$ monoesters and polyesters of sugars and related materials. These esters are derived from a sugar or polyol moiety and one or more carboxylic acid moities. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are $C_{18}$ mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R^3SiO[R^2SiO]_x SiR^3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x [SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R^3SiO[R^2SiO]_x SiR^2OH$ and $HOR^2SiO[R^2SiO]_x SiR^2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are $C_4$–$C_{20}$ alkyl ethers of polypropylene glycols, $C_1$–$C_{20}$ carboxylic acid esters of polypropylene glycols, and di-$C_8$–$C_{30}$ alkyl ethers. Nonlimiting examples of these materials include PPG-14 butyl ether, PPG-15 stearyl ether, dioctyl ether, dodecyl octyl ether, and mixtures thereof.

Nonlimiting examples of conditioning agents useful as water soluble conditioning agents include those selected from the group consisting of polyhydric alcohols, polypropylene glycols, polyethylene glycols, ureas, pyrolidone carboxylic acids, ethoxylated and/or propoxylated $C_3$–$C_6$ diols and triols, alpha-hydroxy $C_2$–$C_6$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG- 26, PPG-30, PPG-34; alkoxylated glucose; hyaluronic acid; and mixtures thereof. Also useful are materials such as aloe vera in any of its variety of forms (e.g., aloe vera gel), chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; and mixtures thereof. Also useful are propoxylated glycerols as described in U.S. Pat. No. 4,976,953, to Orr et al., issued Dec. 11, 1990, which is incorporated by reference herein in its entirety.

The conditioning component preferably used in the present invention may also comprise a conditioning emulsion which is useful for providing a conditioning benefit to the skin or hair during the use of the article. The term "conditioning emulsion" as used herein means the combination of an internal phase comprising a water soluble conditioning agent that is enveloped by an external phase comprising an oil soluble agent. In preferred embodiments, the conditioning emulsion would further comprise an emulsifier. The conditioning emulsion comprises from about 0.25% to about 150%, preferably from about 0.5% to about 100%, and more preferably from about 1% to about 50% by weight of said water insoluble substrate. By a conditioning emulsion is meant a combination of an internal phase comprising a water soluble conditioning agent that is enveloped by an external phase comprising an oil soluble agent. In preferred embodiments, the conditioning emulsion would further comprise an emulsifier.

The conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

The internal phase can optionally comprise other water-soluble or dispersible materials that do not adversely affect the stability of the conditioning emulsion. One such material is a water-soluble electrolyte. The dissolved electrolyte minimizes the tendency of materials present in the lipid phase to also dissolve in the water phase. Any electrolyte capable of imparting ionic strength to the internal phase can be used. Suitable electrolytes include the water soluble mono-, di- or trivalent inorganic salts such as water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the internal phase.

Other water-soluble or dispersible materials that can be present in the internal phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Other water soluble or dispersible materials that can be present in the internal water phase include polycationic polymers to provide steric stabilization at the water-lipid interface and nonionic polymers that also stabilize the water-in-lipid-emulsion. Suitable polycationic polymers include Reten 201, Kymene 557H® and Acco 7112. Suitable nonionic polymers include polyethylene glycols (PEG) such as Carbowax. These polycationic and nonionic polymers will typically be included in a concentration in the range of from about 0.1 to about 1.0% of the internal phase.

Preferred embodiments of the present invention which contain conditioning emulsions comprise an emulsifier capable of forming an emulsion of the internal and external phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from about 0.1% to about 20%, preferably from about 1% to about 10%, and more preferably from about 3% to about 6% by weight of the conditioning emulsion.

The emulsifiers useful in the present invention typically are oil soluble or miscible with the oil soluble external phase materials, especially at the temperature at which the lipid material melts. It also should have a relatively low HLB value. Emulsifiers suitable for use in the present invention have HLB values typically in the range of from about 1 to about 7 and can include mixtures of different emulsifiers. Preferably, these emulsifiers will have HLB values from about 1.5 to about 6, and more preferably from about 2 to about 5.

A wide variety of emulsifiers are useful herein and include, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of $C_{16}$–$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL 6 made by Croda), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Other suitable emulsifiers for use in the present invention include, but is not limited to, glyceryl monoesters, preferably glyceryl monoesters of $C_{16}$–$C_{22}$ saturated, unsaturated and branched chain fatty acids such as glyceryl oleate, glyceryl monostearate, glyceryl monopalmitate, glyceryl monobehenate, and mixtures thereof; polyglyceryl esters of $C_{16}$–$C_{22}$ saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of $C_{16}$–$C_{22}$ saturated, unsaturated and branched chain fatty acids such as methyl glucose dioleate, methyl glucose sesquiisostearate, and mixtures thereof; sucrose fatty acid esters, preferably sucrose esters of $C_{12}$–$C_{22}$ saturated, unsaturated and branched chain fatty acids such as sucrose stearate, sucrose trilaurate, sucrose distearate (e.g., Crodesta® FIO), and mixtures thereof; $C_{12}$–$C_{22}$ ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

In addition to these primary emulsifiers, the compositions of the present invention can optionally contain a coemulsifier to provide additional water-lipid emulsion stability. Suitable coemulsifiers include, but is not limited to, phosphatidyl cholines and phosphatidyl choline-containing compositions such as lecithins; long chain $C_{16}$–$C_{22}$ fatty acid salts such as sodium stearate; long chain $C_{16}$–$C_{22}$ dialiphatic, short chain $C_1$–$C_4$ dialiphatic quaternary ammonium salts such as ditallow dimethyl ammonium chloride and ditallow dimethyl ammonium methylsulfate; long chain $C_{16}$–$C_{22}$ dialkoyl(alkenoyl)-2-hydroxyethyl, short chain $C_1$–$C_4$ dialiphatic quaternary ammonium salts such as ditallowoyl-2-hydroxyethyl dimethyl ammonium chloride; the long chain $C_{16}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain $C_1$–$C_4$ dialiphatic, long chain $C_{16}$–$C_{22}$ monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries).

Weight Ratios and Weight Percentages

In the present invention, the weight ratio of the lathering surfactant to the conditioning component is preferably less than about 40:7, more preferably less than about 5:1, even more preferably less than about 2.5:1, and most preferably less than about 1:1.

In certain preferred embodiments of the present invention, the cleansing and conditioning component, which is defined as comprising a lathering surfactant and a conditioning component further comprising an oil soluble conditioning agent and a water soluble conditioning agent, the lathering surfactant comprises from about 1% to about 75%, preferably from about 10% to about 65%, and more preferably from about 15% to about 45%, by weight of the cleansing and conditioning component, and the conditioning component comprises from about 15% to about 99%, preferably from about 20% to about 75%, and more preferably from about 25% to about 55%, by weight of the cleansing and conditioning component.

Additional Ingredients

The compositions which are added onto or impregnated into the articles of the present invention may comprise a wide range of optional ingredients. Particularly useful are added polymers (as distinct from the polymeric material which may form the substrate), various active ingredients, and cationic surfactants useful for delivering various non-conditioning or non-cleansing benefits of the skin or hair during the cleansing and conditioning process. Additional ingredients of these types are described in greater detail in Procter & Gamble; PCT Application No. WO 99/13861; published Mar. 25, 1999 (P&G Case 6840). This document is incorporated herein by reference.

Other Optional Ingredients

The articles of the present invention can comprise a wide range of other optional components. These additional components should be pharmaceutically acceptable. The CTFA Cosmetic Ingredient Handbook, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

Methods of Manufacture

The disposable, single use personal care cleansing articles of the present invention can be manufactured by separately or simultaneously adding onto or impregnating into a water-insoluble substrate a lathering surfactant and optionally a conditioning component. If necessary, the resulting article can then be dried. By "separately" is meant that the surfactants and conditioning agents can be added sequentially, in any order without first being combined together. By "simultaneously" is meant that the surfactants and conditioning agents can be added at the same time, with or without first being combined together. For the preferred embodiment containing two layers, the lathering surfactant and/or the conditioning component can also be added onto or impregnated into either layers (100 or 200) in any sequence. Alternatively, the lathering surfactant and/or the conditioning component can be added onto or impregnated into the resulting combination of the first layer 100 and the second layer 200. Treatment with the lathering surfactant and/or the conditioning component can be achieved at anytime before or after joining the first layer 100 and the second layer 200. Despite the order of treatment, excess surfactant and/or conditioning component should be removed (e.g., by a nipping process). Thereafter, the treated material (e.g., the first layer 100, the second layer 200, both layers 100 and 200, or joined substrate) should be dried by conventional means.

For example, prior to joining the first layer 100 to the second layer 200, the second layer can be treated with the lathering surfactant. After joining the two layers, either of the outside surfaces (e.g., the unjoined surfaces) of layers 100 and/or 200 can be treated with the conditioning component. Alternatively, the lathering surfactants and conditioning agents can be added onto or impregnated into the second layer 200 at the same time prior to joining the two layers. Alternatively, the lathering surfactants and the conditioning agents can be combined together before adding onto or impregnating into the second layer 200.

Alternatively, prior to joining the two layers, the first layer 100 can be treated with the lathering surfactant employing methods which do not cause the first layer to elongate or extend. This can be achieved in the manufacturing of the first layer or by various application methods well known to those of ordinary skill in the art. Nonlimiting examples of application methods include extrusion coating and slot coating.

The surfactant, conditioning agents, and any optional ingredients can be added onto or impregnated into either layer (100 or 200) or the resulting joined layers (100 and 200) by any means known to those skilled in the art: for example, by spraying, laser printing, splashing, dipping, soaking, or coating.

When water or moisture is used or present in the manufacturing process, the resulting treated substrate is then preferably dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

Preferably, upon wetting with water during use, the articles of the present invention are capable of generating an Average Lather Volume of greater than or equal to about 30 ml, more preferably greater than or equal to about 50 ml, even more preferably greater than or equal to about 75 ml, and most preferably greater than or equal to about 150 ml.

Methods of Cleansing and Conditioning the Skin or Hair

The present invention also relates to a method of cleansing and conditioning the skin or hair with a personal cleansing article of the present invention. These methods comprise the steps of wetting with water a substantially dry, disposable, single use personal cleansing article comprising a water insoluble substrate, a lathering surfactant, and optionally a conditioning component, and contacting the skin or hair with such wetted article. In further embodiments, the present invention is also useful for delivering various active ingredients to the skin or hair.

The articles of the present invention are preferably substantially dry and are intended to be wetted with water prior to use. The article is wetted by immersion in water or by placing it under a stream of water. Lather is generated from the article by mechanically agitating and/or deforming the article either prior to or during contact of the article with the skin or hair. Preferably, upon wetting, the articles of the present invention generate an Average Lather Volume of greater than or equal to about 30 ml, more preferably greater than or equal to about 50 ml, even more preferably greater than or equal to about 75 ml, and most preferably greater than or equal to about 150 ml. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

Without being limited by theory it is believed that the substrate significantly contributes to generation of lather and deposition of conditioning agents and any other active ingredients. It is believed that this increase in lathering and deposition is the result of the surface action of the substrate. As a result, milder and significantly lower amounts of surfactants may be employed. The decreased amount of required surfactant is believed to relate to the decrease in the drying effect of the skin or hair by the surfactants. Furthermore, the diminished amount of surfactant dramatically lowers the inhibitory action (e.g., via emulsification or direct removal by the surfactants) which surfactants exhibit regarding deposition of conditioning agents.

Further without being limited by theory, it is believed that the substrate also enhances deposition of conditioning agents and active ingredients. Since the invention is in dry form, the invention does not require emulsifiers, which can inhibit deposition of conditioning agents and active ingredients. Furthermore, because the skin conditioners and active ingredients are dried onto or impregnated into the substrate, they are transferred directly to the skin or hair by surface contact of the wetted article to the skin.

The substrate also enhances cleansing. The apertured substrate can have differing textures on each side, e.g. a rough side and a smooth side. The apertured substrate acts as an efficient lathering and exfoliating implement. By physically coming into contact with the skin or hair, the substrate significantly aids in cleansing and removal of dirt, makeup, dead skin, and other debris.

Finally, an apertured substrate having at least a portion that is wet extensible provides the desired qualities (e.g., proper texture, thickness, and bulk) of a washcloth. It is also believed that these particular types of apertured substrates enhance lather generation.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name, and all weights are in percent actives.

Examples 1–5

I. The Substrate

A multi-layered substrate, as described in FIGS. 1, 2, 3, 4, 5A, and 5B, is prepared as herein described. The portion of the substrate with the cleansing area is fashioned from non-apertured hydroentangled nonwoven material The second substrate laminated onto the non-apertured substrate is fashioned from a wet-laid process, comprised of 100% pulp. The wet-laid web contains apertures averaging in size about 2–3 mm in diameter, spaced at a frequency of about 3 per cm.

II. The Surfactant Phase

In a suitable vessel, the following ingredients are mixed at room temperature. Add heat as necessary to obtain uniformity.

|  | Weight Percent | | | | |
| --- | --- | --- | --- | --- | --- |
| Ingredients | Example 1 | Example 2 | Example 3 | Example 4 | Example 5 |
| Water | QS 100 | QS 100 | QS 100 | QS 100 | QS 100 |
| Polyquaternium-10 | — | 0.25 | — | — | — |
| PEG 14M | — | 0.5 | 0.5 | — | — |

-continued

| Ingredients | Example 1 | Example 2 | Example 3 | Example 4 | Example 5 |
|---|---|---|---|---|---|
| Hydroxypropyltrimonium Chloride | — | — | — | — | 0.25 |
| Hydroxyethylcellulose | 0.25 | — | — | — | 0.5 |
| Guar Gum | 0.25 | — | — | — | — |

The following are added to the mixture of the above components.

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |
| Glycerin | — | — | — | — | 3.0 |
| Urea | | | | — | 1.0 |

In a separate mixing vessel, the following components are added. The combination is mixed (with heat to 40° C. as necessary) until propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

This mixture is added to the first mixing vessel. About 1.5–2.5 g of the resultant mixture are applied to the hydroentangled non-woven substrate and then dried.

III. Optional Lipid Phase

In a suitable vessel, the following components are mixed with heat until molten (between 75–115° C.).

| | | | | | |
|---|---|---|---|---|---|
| SEFA* Cottonate | 48.00 | 48.00 | 48.00 | 48.00 | 48.00 |
| SEFA* Behenate | 12.00 | — | — | — | — |
| Vitamin E Acetate | — | 2.0 | 2.0 | 2.0 | 2.0 |
| Petrolatum | 10.00 | 10.00 | 10.00 | 10.00 | 23.00 |
| Tribehenin | 5.00 | 5.0 | 5.0 | 5.0 | 5.0 |
| $C_{10}$–$C_{30}$ Cholesterol/ Lanosterol Esters | 25.00 | 23.00 | 23.00 | 23.00 | 10.00 |
| Synthetic Beeswax | — | 3.0 | 3.0 | 3.0 | — |
| Polyethylene Wax | — | 9.0 | 9.0 | 9.0 | — |
| Paraffin | — | — | — | — | 12.00 |
| Amount added to cloth | 0.25 | 0.25 | 0.35 | 0.10 | 0.25 |

*SEFA is an acronym for sucrose esters of fatty acids

The amount of this phase (shown in the above table) is applied to the substrate already containing the materials from the Surfactant and Water-Soluble Conditioner phases, or alternatively, to the wet-laid paper substrate, which is bonded to the hydroentangled substrate with adhesive, as mentioned previously. The lipid phase is applied in a liquid/molten state (e.g., at or above the melting temperature of the resulting lipid mixture) and then cooled. The resulting cleansing article is used by wetting with water and is useful for simultaneously cleansing the skin or hair and depositing the conditioning agents onto the skin or hair in a consistent manner.

Examples 6–10

I. The Substrate

A single-layered hydroentangled/hydroapertured substrate comprising 70% rayon/30% polyester manufactured by PGI (Chicopee 5763) Such a substrate has apertures of about 2 mm dispersed within it at a frequency of about 3 apertures per centimeter.

II. The Surfactant Phase

In a suitable vessel, the following components are mixed at room temperature. The mixture is heated as necessary to obtain uniformity.

| Ingredients | Example 6 | Example 7 | Example 8 | Example 9 | Example 10 |
|---|---|---|---|---|---|
| Water | QS 100 | QS 100 | QS 100 | QS 100 | QS 100 |
| Polyquaternium-10 | — | 0.25 | — | — | — |
| PEG14M | — | 0.5 | 0.5 | — | — |
| Hydroxypropyltrimonium Chloride | — | — | — | — | 0.25 |
| Hydroxyethylcellulose | 0.25 | — | — | — | 0.5 |
| Guar Gum | 0.25 | — | — | — | — |

The following components are added to the mixture of the above components

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |
| Glycerin | — | — | — | — | 3.0 |
| Urea | | | | — | 1.0 |

In a separate mixing vessel, the following components are added. The combination is mixed (with heat to 40° C. as necessary) until propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

This mixture is added to the first mixing vessel. About 1.5–2.5 g of the resultant mixture are added to the non-woven substrate and then dried.

III. Optional Conditioning Emulsion.

In a suitable vessel, the following ingredients are mixed with heat until molten (between 75–115° C.).

| | | | | | |
|---|---|---|---|---|---|
| SEFA* Cottonate | 27.36 | 27.36 | 27.36 | 27.36 | 27.36 |
| SEFA* Behenate | 6.84 | — | — | 6.84 | — |
| Polyethylene Wax | — | 5.13 | 6.84 | — | — |
| Synthetic Beeswax | — | 1.71 | — | — | — |
| Petrolatum | 5.7 | 5.7 | 5.7 | 5.7 | 13.1 |
| C10–C30 cholesterol/ lanosterol esters | 13.1 | 13.1 | 13.1 | 13.1 | 5.7 |

-continued

| | | | | | |
|---|---|---|---|---|---|
| Vitamin E Acetate | 1.14 | 1.14 | 1.14 | 1.14 | 1.14 |
| Tribehenin | 2.85 | 2.85 | 2.85 | 2.85 | 2.85 |
| Decaglyceryl Dipalmitate | 0.3 | — | 0.3 | 0.3 | — |
| Triglyceryl Monostearate | 2.7 | 0.3 | 2.7 | 2.7 | 0.3 |
| Decaglyceryl Stearate | — | 2.7 | — | — | 2.7 |
| Polyglyceryl Tristearate | — | — | — | — | — |

*SEFA is an acronym for sucrose esters of fatty acids

The following components are then mixed together at room temperature until homogeneous. Once the mixture above is completely melted, heating is stopped and slowly the following components are added while continuing to mix:

| | | | | | |
|---|---|---|---|---|---|
| Water | — | — | 5.0 | 6.0 | 5.0 |
| Glycerin | 35.0 | 30.0 | 25.0 | 25.0 | 21.0 |
| Dex Panthenol | — | 5.0 | 3.0 | 2.0 | 2.0 |
| Urea | — | 1.0 | — | 2.0 | 1.0 |
| PEG-30 | — | 4.0 | 2.0 | 2.0 | 5.0 |
| Propylene glycol | — | — | 4.0 | 3.0 | 5.75 |
| Polyquaternium-10 | — | — | 1.0 | — | 0.25 |

About 0.1–1.0 g of this phase in a liquid/molten state is added to the substrate already containing the materials from the Surfactant Phase. The combination is cooled to room temperature (about 20° C.) after application. The resulting cleansing and conditioning article is used by wetting with water and is useful for cleansing the skin or hair and for depositing the conditioning emulsions onto the skin or hair.

Examples 11, 12 and Comparative

The following additional examples further describe and demonstrate embodiments within the scope of the present invention and document the effect of aperture size and frequency on lathering performance.

I. The Substrate

Substrates consist of carded, hydroentangled non-wovens comprised of 70% rayon and 30% polyester. Materials are very close in all properties, ranging from 67–75 grams per square meter, with the only variable being aperture size and aperture frequency.

| | Description | | |
|---|---|---|---|
| Substrate | Example 11 | Example 12 | Comparative Example |
| Supplier | Polymer Group Chicopee Division | Veratec (now BBA) | Dupont |
| Identification Number | Chicopee C5763 | H140-102 | 8423 |
| Basis Weight (grams per square meter) | 70 | 67 | 75 |
| Aperture Size (diameter, mm) | 2 | 1 | 0* |
| Aperture frequency (#/inch) | 8 | 20 | N/A* |

*Non-apertured substrate. Some very small holes can be seen but are too small to measure.

II. The Surfactant Phase

In a suitable vessel, the following ingredients are mixed at room temperature. Heat is added as necessary to obtain uniformity.

| | Weight Percent | | |
|---|---|---|---|
| Ingredients | Example 11 | Example 12 | Comparative Example |
| Water | QS 100 | QS 100 | QS 100 |
| Polyquaternium-10 | 0.25 | 0.25 | 0.25 |
| PEG 14M | 0.5 | 0.5 | 0.5 |

The following components are added to the mixture of the above components.

| | | | |
|---|---|---|---|
| Disodium EDTA | 0.10 | 0.10 | 0.10 |
| Sodium Lauroyl Sarcosinate | 3.33 | 3.33 | 3.33 |
| Cocamidopropyl Betaine | 3.33 | 3.33 | 3.33 |
| Decyl Polyglucoside | 3.33 | 3.33 | 3.33 |
| Methyl Paraben | 0.25 | 0.25 | 0.25 |
| Phenoxyethanol | 0.3 | 0.3 | 0.3 |
| Benzyl Alcohol | 0.3 | 0.3 | 0.3 |

In a separate mixing vessel, the following components are added. The combination is mixed (with heat to 40° C. as necessary) until propyl paraben is dissolved.

| | | | |
|---|---|---|---|
| Water | 2.0 | 2.0 | 2.0 |
| Butylene Glycol | 2.0 | 2.0 | 2.0 |
| Propyl Paraben | 0.15 | 0.15 | 0.15 |

This mixture is added to the first mixing vessel. About 2.0 grams of the resultant mixture are added to a non-woven substrate and then dried.

Lather Performance Data

Delivering lather quickly is critical to cleansing perception and performance as well as ease of use for personal cleansing articles in substrate form. The following method is used to evaluate differences in lather characteristics, specifically how much lather the treated substrate delivers in a short time period (flash lather volume). The method involves generation of lather by panelists.

Instructions/Protocol:

All measurements are conducted with water temperature at 95° C.
Wash hands with Ivory bar before starting test. A wash with Ivory bar is also done between products to remove oil/dirt or residue from previous cleansers.
1) Crumple up the dry substrate product in hand (into a ball).
2) Add 10 ml water at 95° C. to wet the substrate product.
3) Activate lather by rubbing the substrate in circular motion between the hands for 6 seconds.
4) Gather lather and scrape into 250 ml beaker.
5) Repeat Step (4) four more times (total of 5 reps).
6) Discard the product.

7) Determine the amount of lather in the beaker to the nearest 5 ml.
6) Report the amount of lather measured as Flash Volume.

| | Lather Performance | | |
|---|---|---|---|
| Substrate | Example 11 | Example 12 | Comparative Example |
| Flash Lather Volume (ml) | 175 | 125 | 100 |

It can be seen from the Flash Lather Volume data that the use of an apertured substrate helps generate lather for the articles of the present invention in comparison with a similar article that is prepared from a non-apertured substrate.

Examples 13–15

I. The Substrate

Substrates consist of composite or laminate material where at least one of the two materials is apertured to improve lather formation, as observed in the previous set of examples. The apertured and non-apertured substrate materials can consist of various types of non-woven webs (carded, hydroentangled, meltblown, spunbond, SMS, etc.) and/or wet laid paper webs.

| | Description | | |
|---|---|---|---|
| Substrate | Example 13 Non apertured + apertured | Example 14 Apertured + Apertured | Example 15 Non-apertured + Apertured |
| Substrate 1 | PGI 9950 50/50 rayon/polyester 50 gsm. Hydroentangled, non-apertured | Veratec H140-102 Hydroentangled/ hydroapertured web 70/30 rayon/polyester 67 gsm 20 apertures/inch 1 mm diameter | 100% wet laid paper 40 gsm non-apertured |
| Substrate 2 | Apertured wet laid paper 31 gsm. 2–3 mm diameter 3 apertures/cm | Apertured wet laid paper 31 gsm. 2–3 mm diameter 3 apertures/cm | Apertured wet laid paper 31 gsm. 2–3 mm diameter 3 apertures/cm |

In each instance, Substrate 1 is pattern bonded to Substrate 2 in a configuration similar to that exhibited in FIG. 1 of the drawings.

II. The Surfactant Phase

In a suitable vessel, the following ingredients are mixed at room temperature. Heat is added as necessary to obtain uniformity.

| | Weight Percent | | |
|---|---|---|---|
| Ingredients | Example 13 | Example 14 | Example 15 |
| Water | QS 100 | QS 100 | QS 100 |
| Polyquaternium-10 | 0.25 | 0.25 | 0.25 |
| PEG 14M | 0.5 | 0.5 | 0.5 |
| Disodium EDTA | 0.10 | 0.10 | 0.10 |
| Sodium Lauroyl Sarcosinate | 3.33 | 3.33 | 3.33 |
| Cocamidopropyl Betaine | 3.33 | 3.33 | 3.33 |
| Decyl Polyglucoside | 3.33 | 3.33 | 3.33 |
| Methyl Paraben | 0.25 | 0.25 | 0.25 |
| Phenoxyethanol | 0.3 | 0.3 | 0.3 |
| Benzyl Alcohol | 0.3 | 0.3 | 0.3 |

The following components are added to the mixture of the above components.

In a separate mixing vessel, the following components are added. The components are then mixed (with heat to 40° C. as necessary) until propyl paraben is dissolved.

| Water | 2.0 | 2.0 | 2.0 |
|---|---|---|---|
| Butylene Glycol | 2.0 | 2.0 | 2.0 |
| Propyl Paraben | 0.15 | 0.15 | 0.15 |

This mixture is then added to the first mixing vessel. About 2.5 grams of the resultant mixture are added to the non-woven/paper composites to form cleansing articles of the present invention.

What is claimed is:

1. A disposable, single use, personal cleansing article for cleansing and conditioning the skin, said personal cleansing article being water-activated during use to generate lather, said article comprising:
   (a) a water-insoluble substrate having at least one cleansing surface containing a plurality of apertures, said apertures ranging in average size from about 0.5 to about 12 mm in diameter and being located within said cleansing surface of said substrate at a frequency of from about 0.5 to about 12 per linear centimeter;
   (b) from about 0.5% to about 250% by weight of said substrate of a lathering surfactant releasably associated with said substrate; and
   (c) from 0.01% to about 99% by weight of said substrate of a conditioning component added onto or impregnated into said substrate, wherein said conditioning component comprises petrolatum;
wherein the substrate is a nonwoven substrate comprised of fibers.

2. The article of claim 1 wherein said article is substantially dry.

3. The article of claim 1 wherein said personal cleansing article generates an average lather volume of greater than 30 mls upon wetting.

4. The article of claim 1 wherein said personal cleansing article generates an average lather volume of greater than 75 mls upon wetting.

5. The article of claim 1 wherein said personal cleansing article generates an average lather volume of greater than 90 mls upon wetting.

6. The article of claim 1 wherein the nonwoven substrate is a single ply substrate.

7. The article of claim 1 wherein said apertures range in average size from about 1 to about 4 mm in diameter.

8. The article of claim 7 wherein said apertures range in average size from about 2 to about 4 mm in diameter.

9. The article of claim 5 wherein the apertures are located within said cleansing surface of said substrate at a frequency of from about 1.5 to about 6 per linear centimeter.

10. The article of claim 5 wherein the apertures are located within said cleansing surface of said substrate at a frequency of from about 3 to about 6 per linear centimeter.

11. The article of claim 5 wherein the apertures are uniformly distributed within said cleansing surface of said substrate.

12. The article of claim 5 wherein the conditioning component is present at a level ranging from 0.1% to 50% by weight of the substrate.

13. The article of claim 12 wherein the conditioning component is present at a level ranging from 1% to 25% by weight of the substrate.

14. The article of claim 5 wherein the conditioning component comprises an oil soluble conditioning component and a water soluble conditioning component wherein the oil soluble conditioning component comprises petrolatum and wherein the water soluble conditioning component comprises glycerin.

15. The article of claim 5 which additionally comprises cationic polymer at a level ranging from about 0.1% to about 1% by weight of the substrate.

16. The article of claim 5 wherein the apertures protrude completely through the substrate to the surface of the substrate which is opposite to the cleansing surface.

17. The article of claim 5 wherein the conditioning component comprises an oil soluble conditioning component which consists essentially of petrolatum.

18. The article of claim 17 wherein the conditioning component additionally comprises a water soluble conditioning component.

19. The article of claim 18 wherein the water soluble conditioning component comprises glycerin.

20. The article of claim 5 wherein the nonwoven substrate consists essentially of fibers.

21. The article of claim 1 wherein the nonwoven substrate has a basis weight of from about 24 to about 96 gsm.

22. The article of claim 21 wherein the nonwoven substrate has a basis weight of from about 36 to about 84 gsm.

23. The article of claim 22 wherein the nonwoven substrate has a basis weight of from about 42 to about 78 gsm.

24. The article of claim 1 wherein the fibers of the nonwoven substrate are selected from the group consisting of polyester, rayon, and mixture thereof.

25. The article of claim 1 wherein the nonwoven substrate is hydroentangled.

26. The article of claim 1 wherein the article comprises from about 1% to about 250%, by weight of the substrate, of the lathering surfactant.

27. The article of claim 26 wherein the article comprises from about 10% to about 250%, by weight of the substrate, of the lathering surfactant.

28. The article of claim 1 wherein the lathering surfactant is selected from the group consisting of alkyl glucoside, cocamidopropyl betaine, sodium lauroyl sarcosinate, sodium lauroyl lactylate, sodium laureth sulfate, and mixtures thereof.

29. The article of claim 1 wherein the conditioning component further comprises a material selected from the group consisting of glycerin, cholesterol urea, butylene glycol, propylene glycol, and mixtures thereof.

30. The article of claim 1 wherein the article further comprises a material selected from the group consisting of polyquaternium-10, vitamin E acetate, fragrance, methyl glucose dioleate, disodium EDTA, methylparaben, propylparaben, colorant, and mixtures thereof.

31. The article of claim 1 wherein the lathering surfactant is alkyl glucoside, cocamidopropyl betaine, sodium lauroyl sarcosinate, and sodium lauroyl lactylate; and wherein the article further comprises polyquaternium-10, vitamin E acetate, cholesterol, urea, fragrance, and butylene glycol.

32. The article of claim 31 wherein the apertures range in average size from about 1 to about 4 mm in diameter.

33. The article of claim 31 wherein the fibers of the nonwoven substrate are selected from the group consisting of polyester, rayon, and mixtures thereof.

34. The article of claim 31 wherein the nonwoven substrate is a single ply substrate.

35. The article of claim 31 wherein the nonwoven substrate is hydroentangled.

36. The article of claim 31 wherein the article is substantially dry.

37. The article of claim 31 wherein the article generates an average lather volume of greater than 75 mls upon wetting.

38. The article of claim 31 wherein the article comprises from about 10% to about 250%, by weight of the substrate, of the lathering surfactant.

39. The article of claim 1 wherein the lathering surfactant is alkyl glucoside, cocamidopropyl betaine, and sodium laureth sulfate; and wherein the article further comprises fragrance, methyl glucose dioleate, disodium EDTA, propylene glycol, methylparaben, propylparaben, and colorant.

40. The article of claim 39, wherein the apertures range in average size from about 1 to about 4 mm in diameter.

41. The article of claim 39 wherein the fibers of the nonwoven substrate are selected from the group consisting of polyester, rayon, and mixtures thereof.

42. The article of claim 39 wherein the nonwoven substrate is a single ply substrate.

43. The article of claim 39 wherein the nonwoven substrate is hydroentangled.

44. The article of claim 39 wherein the article is substantially dry.

45. The article of claim 39 wherein the article generates an average lather volume of greater than 75 mls upon wetting.

46. The article of claim 39 wherein the article comprises from about 10% to about 250%, by weight of the substrate, of the lathering surfactant.

47. The article of claim 1 wherein the lathering surfactant is sodium laureth sulfate; and wherein the article further comprises fragrance, disodium EDTA, and methylparaben.

48. The article of claim 47, wherein the apertures range in average size from about 1 to about 4 mm in diameter.

49. The article of claim 47 wherein the fibers of the nonwoven substrate are selected from the group consisting of polyester, rayon, and mixtures thereof.

50. The article of claim 47 wherein the nonwoven substrate is a single ply substrate.

51. The article of claim 47 wherein the nonwoven substrate is hydroentangled.

52. The article of claim 47 wherein the article is substantially dry.

53. The article of claim 47 wherein the article generates an average lather volume of greater than 75 mls upon wetting.

54. The article of claim 47 wherein the article comprises from about 10% to about 250%, by weight of the substrate, of the lathering surfactant.

* * * * *